(12) United States Patent
Janne et al.

(10) Patent No.: US 10,865,451 B2
(45) Date of Patent: Dec. 15, 2020

(54) NON-INVASIVE BLOOD BASED MONITORING OF GENOMIC ALTERATIONS IN CANCER

(71) Applicant: Dana-Farber Cancer Institute, Inc., Boston, MA (US)

(72) Inventors: Pasi A. Janne, Needham, MA (US); Cloud P. Paweletz, Boston, MA (US); Geoffrey Oxnard, Arlington, MA (US); Yanan Kuang, Belmont, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 22 days.

(21) Appl. No.: 14/897,269

(22) PCT Filed: Jun. 11, 2014

(86) PCT No.: PCT/US2014/041871
§ 371 (c)(1),
(2) Date: Dec. 10, 2015

(87) PCT Pub. No.: WO2014/201092
PCT Pub. Date: Dec. 18, 2014

(65) Prior Publication Data
US 2016/0138112 A1    May 19, 2016

Related U.S. Application Data

(60) Provisional application No. 61/833,556, filed on Jun. 11, 2013, provisional application No. 61/889,148, filed on Oct. 10, 2013.

(51) Int. Cl.
| | |
|---|---|
| *C12Q 1/68* | (2018.01) |
| *C12P 19/34* | (2006.01) |
| *C12Q 1/6886* | (2018.01) |
| *C12Q 1/6827* | (2018.01) |
| *A61K 31/437* | (2006.01) |
| *A61K 31/517* | (2006.01) |

(52) U.S. Cl.
CPC .......... *C12Q 1/6886* (2013.01); *A61K 31/437* (2013.01); *A61K 31/517* (2013.01); *C12Q 1/6827* (2013.01); *C12Q 2600/106* (2013.01); *C12Q 2600/156* (2013.01)

(58) Field of Classification Search
CPC ............ C12Q 1/6827; C12Q 2545/101; C12Q 1/6886; C12Q 2600/106; C12Q 2600/156
See application file for complete search history.

(56) References Cited

U.S. PATENT DOCUMENTS

| 2009/0181378 A1 | 7/2009 | Sanders et al. |
| 2009/0280479 A1 | 11/2009 | Hoon et al. |
| 2013/0029339 A1 | 1/2013 | Skog et al. |

OTHER PUBLICATIONS

Schmid K. et al .Clin Cancer Res 2009;15(14) p. 4554-4560.*
So, A. et al. Abstract 3399: Detection of rare mutations in plasma by droplet digital PCR, AACR; Cancer Res 2012;72(8 Suppl): Abstract nr 3399.*
Magnin, S. et al, The Journal of Molecular Diagnostics, vol. 13, No. 5, Sep. 2011.*
Lurkin I, Stoehr R, Hurst CD, van Tilborg AAG, Knowles MA, et al. (2010) Two Multiplex Assays That Simultaneously Identify 22 Possible Mutation Sites in the KRAS, BRAF, NRAS and PIK3CA Genes. PLoS One.*
Ercolani, L. et al. "Isolation and Complete Sequence of a Functional Human Glyceraldehyde-3-phosphate Dehydrogenase Gene" The Journal of Biological Chemistry, vol. 263, No. 30, Issue of Oct. 25, pp. 15335-15341. (Year: 1988).*
Pickeral. O.K. et al. Frequent Human Genomic DNA Transduction Driven by Line-1 Retrotransposition, Genome Research, 10:411-415 (Year: 2000).*
PCT/US2014/041871, Oct. 24, 2014, International Search Report and Written Opinion.
PCT/US2014/041871, Dec. 23, 2015, International Preliminary Report on Patentability.
International Search Report and Written Opinion for PCT/US2014/041871 dated Oct. 24, 2014.
International Preliminary Report on Patentability for PCT/US2014/041871 dated Dec. 23, 2015.
Arcila et al., Rebiopsy of lung cancer patients with acquired resistance to EGFR inhibitors and enhanced detection of the T790M mutation using a locked nucleic acid-based assay. Clin Cancer Res. Mar. 1, 2011;17(5):1169-80.doi: 10.1158/1078-0432.CCR-10-2277. Epub Jan. 19, 2011.

(Continued)

*Primary Examiner* — Stephen T Kapushoc
(74) *Attorney, Agent, or Firm* — Wolf, Greenfield & Sacks, P.C.

(57) ABSTRACT

The invention provides methods to monitor cell free nucleic acids. The method comprises obtaining a plasma sample from a subject known to have a cancer characterized by a pair of mutually exclusive mutations specific to the cancer; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; and indicating in a report that the subject has the first mutation when (a) the amount of the housekeeping gene and/or total DNA in the cell free nucleic acids isolated from the plasma sample is within the selected range and (b) the amount of the first mutation is increased as compared to a control amount, wherein the control amount is determined by measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject.

26 Claims, 26 Drawing Sheets

Specification includes a Sequence Listing.

(56) References Cited

OTHER PUBLICATIONS

Barlesi et al., Biomarkers (BM) France: Results of routine EGFR, HER2, KRAS, BRAF, PI3KCA mutations detection and EML4-ALK gene fusion assessment on the first 10,000 non-small cell lung cancer (NSCLC) patients (pts). J Clin Oncol. 2013;31: Abstract 8000.

Branford et al., Initial molecular response at 3 months may predict both response and event-free survival at 24 months in imatinib-resistant or -intolerant patients with Philadelphia chromosome-positive chronic myeloid leukemia in chronic phase treated with nilotinib. J Clin Oncol. Dec. 10, 2012;30(35):4323-9. doi:10.1200/JCO.2011.40.5217. Epub Oct. 29, 2012.

Cancer Genome Atlas Research Network. Comprehensive genomic characterization defines human glioblastoma genes and core pathways. Nature. Oct. 23, 2008;455(7216):1061-8. doi: 10.1038/nature07385. Epub Sep. 4, 2008. Erratum in: Nature. Feb. 28, 2013;494(7438):506.

Cancer Genome Atlas Research Network. Integrated genomic analyses of ovarian carcinoma. Nature. Jun. 29, 2011;474(7353):609-15. doi: 10.1038/nature10166. Erratum in: Nature. Oct. 11, 2012;490(7419):298.

Cardarella et al., Clinical, pathologic, and biologic features associated with BRAF mutations in non-small cell lung cancer. Clin Cancer Res. Aug. 15, 2013;19(16):4532-40. doi: 10.1158/1078-0432.CCR-13-0657. Epub Jul. 5, 2013.

Cardarella et al., The introduction of systematic genomic testing for patients with non-small-cell lung cancer. J Thorac Oncol. Dec. 2012;7(12):1767-74. doi: 10.1097/JTO.0b013e3182745bcb.

Ciriello et al., Mutual exclusivity analysis identifies oncogenic network modules. Genome Res. Feb. 2012;22(2):398-406. doi:10.1101/gr.125567.111. Epub Sep. 9, 2011.

Cui, A network of cancer genes with co-occurring and anti-co-occurring mutations. PLoS One. Oct. 4, 2010;5(10). pii: e13180. doi:10.1371/journal.pone.0013180.

Dawson et al., Analysis of circulating tumor DNA to monitor metastatic breast cancer. N Engl J Med. Mar. 28, 2013;368(13):1199-209. doi:10.1056/NEJMoa1213261. Epub Mar. 13, 2013.

Diaz et al., The molecular evolution of acquired resistance to targeted EGFR blockade in colorectal cancers. Nature. Jun. 28, 2012;486(7404):537-40. doi: 10.1038/nature11219.

Flaherty et al., Inhibition of mutated, activated BRAF in metastatic melanoma. N Engl J Med. Aug. 26, 2010;363(9):809-19. doi:10.1056/NEJMoa1002011.

Higgins et al., Detection of tumor PIK3CA status in metastatic breast cancer using peripheral blood. Clin Cancer Res. Jun. 15, 2012;18(12):3462-9. doi:10.1158/1078-0432.CCR-11-2696. Epub Mar. 15, 2012.

Hindson et al., High-throughput droplet digital PCR system for absolute quantitation of DNA copy number. Anal Chem. Nov. 15, 2011;83(22):8604-10. doi: 10.1021/ac202028g. Epub Oct. 28, 2011.

Jackman et al., Impact of epidermal growth factor receptor and KRAS mutations on clinical outcomes in previously untreated non-small cell lung cancer patients: results of an online tumor registry of clinical trials. Clin Cancer Res. Aug. 15, 2009;15(16):5267-73. doi: 10.1158/1078-0432.CCR-09-0888. Epub Aug. 11, 2009.

Johnson et al., Association of KRAS and EGFR mutations with survival in patients with advanced lung adenocarcinomas. Cancer. Jan. 15, 2013;119(2):356-62. doi: 10.1002/cncr.27730. Epub Jul. 18, 2012.

Karapetis et al., K-ras mutations and benefit from cetuximab in advanced colorectal cancer. N Engl J Med. Oct. 23, 2008;359(17):1757-65. doi:10.1056/NEJMoa0804385.

Kuang et al., Noninvasive detection of EGFR T790M in gefitinib or erlotinib resistant non-small cell lung cancer. Clin Cancer Res. Apr. 15, 2009;15(8):2630-6. doi: 10.1158/1078-0432.CCR-08-2592. Epub Apr. 7, 2009.

Kwak et al., Anaplastic lymphoma kinase inhibition in non-small-cell lung cancer. N Engl J Med. Oct. 28, 2010;363(18):1693-703. doi:10.1056/NEJMoa1006448. Erratum in: N Engl J Med. Feb. 10, 2011;364(6):588.

Leary et al., Detection of chromosomal alterations in the circulation of cancer patients with whole-genome sequencing. Sci Transl Med. Nov. 28, 2012;4(162):162ra154. doi:10.1126/scitranslmed.3004742.

Maheswaran et al., Detection of mutations in EGFR in circulating lung-cancer cells. N Engl J Med. Jul. 24, 2008;359(4):366-77. doi: 10.1056/NEJMoa0800668. Epub Jul. 2, 2008.

Misale et al., Emergence of KRAS mutations and acquired resistance to anti-EGFR therapy in colorectal cancer. Nature. Jun. 28, 2012;486(7404):532-6. doi: 10.1038/nature11156.

Mok et al., Detection of EGFR-activating mutations from plasma DNA as a potent predictor of survival outcomes in FASTACT 2: A randomized phase III study on intercalated combination of erlotinib (E) and chemotherapy (C). J Clin Oncol. 2013;31: Abstract 8021.

Oxnard et al., Acquired resistance to EGFR tyrosine kinase inhibitors in EGFR-mutant lung cancer: distinct natural history of patients with tumors harboring the T790M mutation. Clin Cancer Res. Mar. 15, 2011;17(6):1616-22. doi:10.1158/1078-0432.CCR-10-2692. Epub Dec. 6, 2010.

Oxnard et al., Noninvasive detection of response and resistance in EGFR-mutant lung cancer using quantitative next-generation genotyping of cell-free plasma DNA. Clin Cancer Res. Mar. 15, 2014;20(6):1698-705. doi: 10.1158/1078-0432.CCR-13-2482. Epub Jan. 15, 2014.

Paez et al., EGFR mutations in lung cancer: correlation with clinical response to gefitinib therapy. Science. Jun. 4, 2004;304(5676):1497-500. Epub Apr. 29, 2004.

Rago et al., Serial assessment of human tumor burdens in mice by the analysis of circulating DNA. Cancer Res. Oct. 1, 2007;67(19):9364-70.

Sacher et al., Noninvasive prediction of lung cancer acquired resistance genotype using droplet digital PCR analysis of cell-free plasma DNA. Annual Meeting. May 30, 2014, Chicago, Illinois. Poster Presentation.

Sacher et al., Prediction of lung cancer genotype noninvasively using droplet digital PCR (ddPCR) analysis of cell-free plasma DNA (cfDNA). ASCO Annual Meeting. May 30, 2014, Chicago, Illinois. Abstract.

Sequist et al., First-in-human evaluation of CO-1686, an irreversible, selective, and potent tyrosine kinase inhibitor of EGFR T790M. J Clin Oncol May 20, 2013;31(15): Abstract 2524.

Spindler et al., Quantitative cell-free DNA, KRAS, and BRAF mutations in plasma from patients with metastatic colorectal cancer during treatment with cetuximab and irinotecan. Clin Cancer Res. Feb. 15, 2012;18(4):1177-85. doi: 10.1158/1078-0432.CCR-11-0564. Epub Jan. 6, 2012.

Vogelstein et al., Digital PCR. Proc Natl Acad Sci U S A. Aug. 3, 1999;96(16):9236-41.

Zhou et al., Novel mutant-selective EGFR kinase inhibitors against EGFR T790M. Nature. Dec. 24, 2009;462(7276):1070-4. doi: 10.1038/nature08622.

Zhou et al., Relative abundance of EGFR mutations predicts benefit from gefitinib treatment for advanced non-small-cell lung cancer. J Clin Oncol. Aug. 20, 2011;29(24):3316-21. doi:10.1200/JCO.2010.33.3757. Epub Jul. 25, 2011.

Extended European Search Report for EP 14811186.7 dated Dec. 12, 2016.

Kim et al., Can mutations of EGFR and KRAS in serum be predictive and prognostic markers in patients with advanced non-small cell lung cancer (NSCLC)? Med Oncol. Mar. 2013;30(1):328. doi:10.1007/s12032-012-0328-3.

Pennycuick et al., Routine EGFR and KRAS Mutation analysis using Cold-PCR in non-small cell lung cancer. Int J Clin Pract. Aug. 2012;66(8):748-752. doi:10.1111/j.1742-1241.2012.02961.x.

Wang et al., Quantifying EGFR alterations in the lung cancer genome with nanofluidic digital PCR arrays. Clin Chem. Apr. 2010;56(4):623-32. doi: 10.1373/clinchem.2009.134973.

(56) References Cited

OTHER PUBLICATIONS

Benesova et al., Mutation-based detection and monitoring of cell-free tumor DNA in peripheral blood of cancer patients. Anal Biochem. Feb. 15, 2013;433(2):227-34. doi: 10.1016/j.ab.2012.06.018. Epub Jun. 28, 2012.

Park et al., MYC quantitation in cell-free plasma DNA by real-time PCR for gastric cancer diagnosis. Clin Chem Lab Med. 2009;47(5):530-6. doi: 10.1515/CCLM.2009.126. Abstract Only.

* cited by examiner

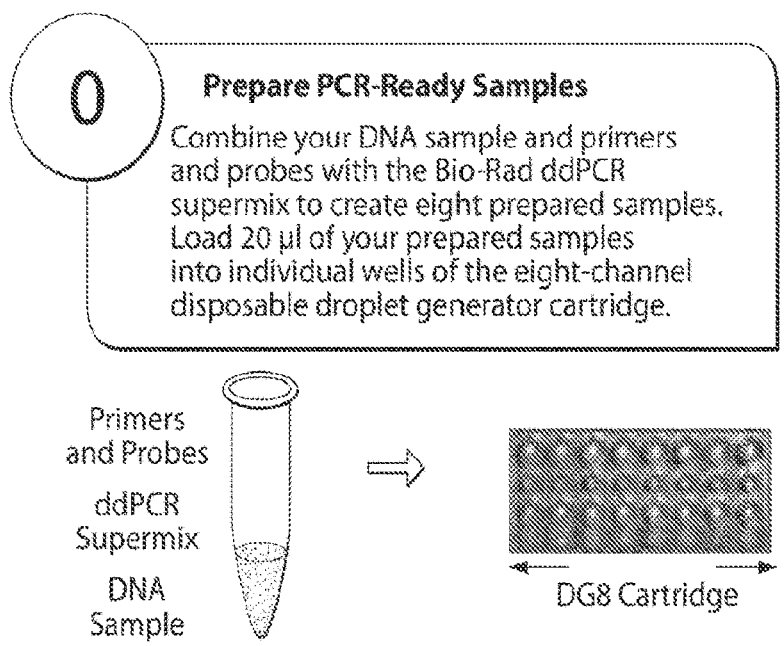
Fig. 7-1
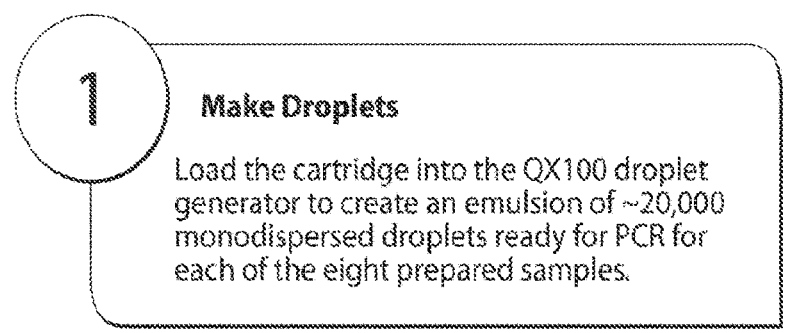
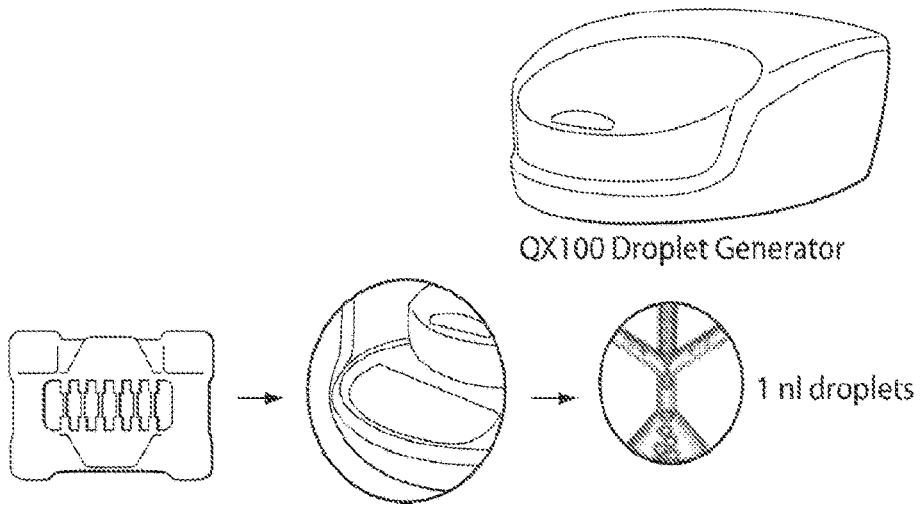
Fig. 7-2

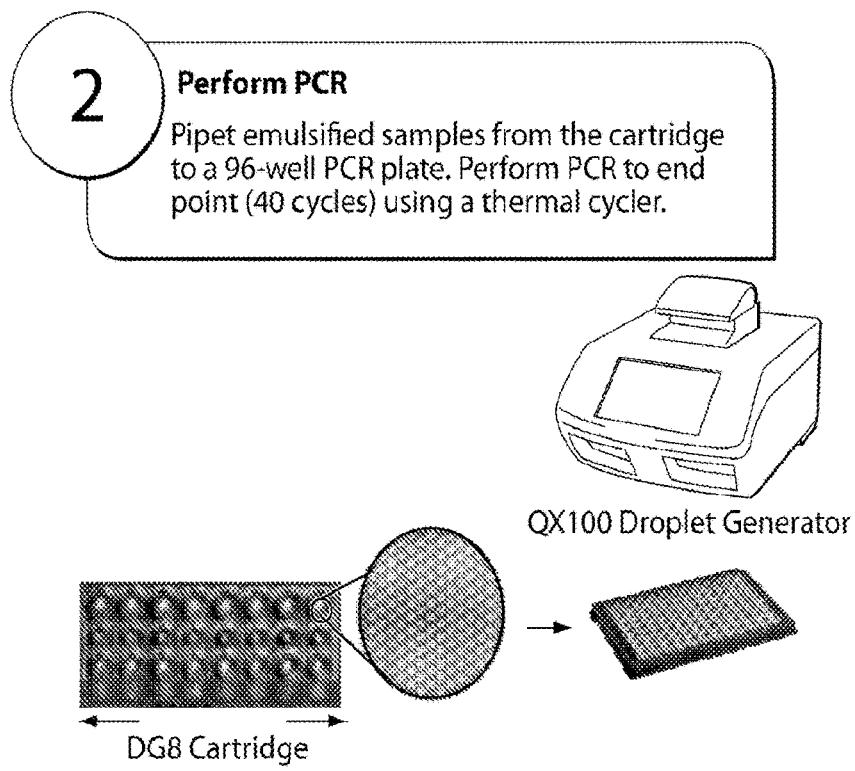
Fig. 7-3
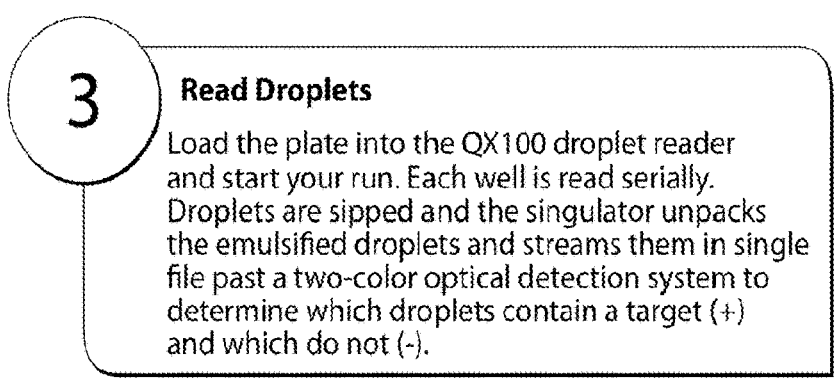
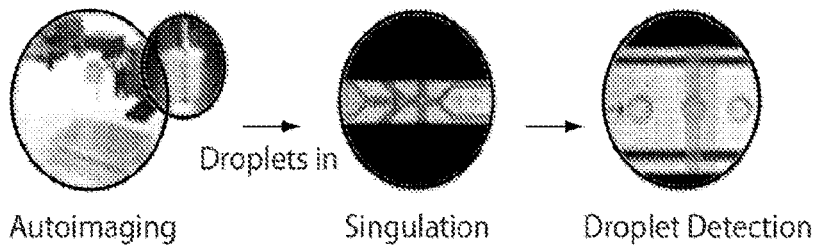
Fig. 7-4

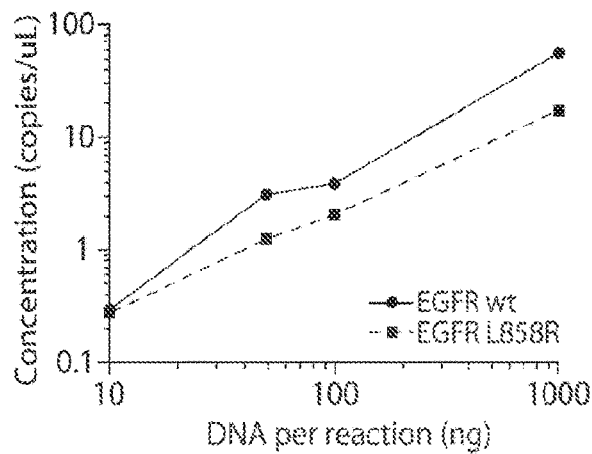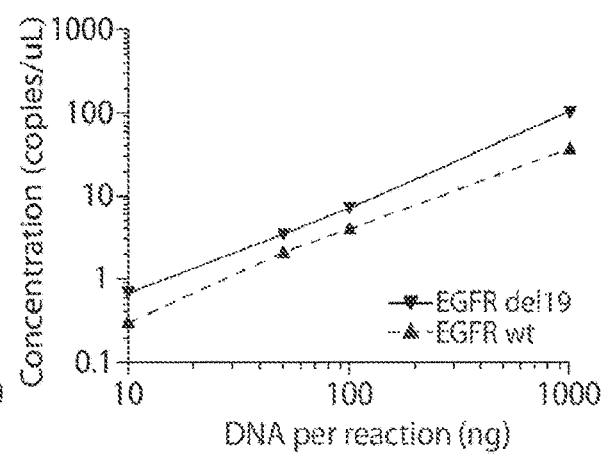
Fig. 13A    Fig. 13B
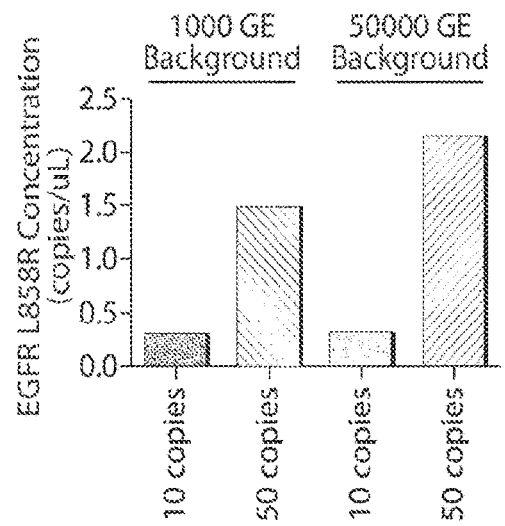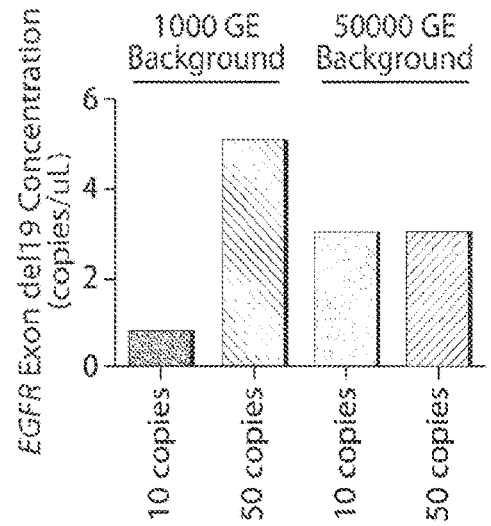
Fig. 13C    Fig. 13D

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1
gtgagaaagt taaaattccc gtc                                              23

```
<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
cacacagcaa agcagaaac                                                    19

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
aggaattaag agaagcaaca tc                                                22

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
atcgaggatt tccttgttg                                                    19
```

NON-INVASIVE BLOOD BASED MONITORING OF GENOMIC ALTERATIONS IN CANCER

RELATED APPLICATIONS

This application is a national stage filing under 35 U.S.C. § 371 of International Application No. PCT/US2014/041871, filed Jun. 11, 2014, and entitled "NON-INVASIVE BLOOD BASED MONITORING OF GENOMIC ALTERATIONS IN CANCER," which claims priority under 35 U.S.C. § 119(e) to U.S. Provisional Patent Applications 61/889,148, filed on Oct. 10, 2013 and 61/833,556, filed on Jun. 11, 2013, each of which are incorporated herein in their entirety.

FEDERALLY SPONSORED RESEARCH

This invention was made with government support under grant numbers P50 CA090578 and R01 CA135257 awarded by The National Institutes of Health. The government has certain rights in the invention.

FIELD OF THE INVENTION

The present invention relates in general to cancer. More specifically, the invention relates to methods monitoring cell free DNA for performing disease monitoring and pharmacodynamic assessment of drug efficacy.

BACKGROUND OF THE INVENTION

Cancer remains a major health concern. Despite increased understanding of many aspects of cancer, the methods available for its treatment continue to have limited success. A major limitation in current cancer therapy is a lack of understanding of the molecular changes in cancers in response to therapies. This is particularly exemplified for cancers such as epidermal growth factor receptor (EGFR) mutant lung cancer or BRAF mutant melanoma, where despite initial dramatic clinical efficacy of erlotinib or vermurafenib, drug resistance to these targeted therapies ultimately develops in all patients. An understanding of when and how this occurs may help guide subsequent therapeutic choices.

The challenges of genotype-directed cancer care are mostly driven by the inability to get repeat biopsies from the same patients. Thus, performing genotyping of tumors using body fluids, such as blood is desirable. However, blood has very low concentrations of the DNA fragments of interest (that is derived from the tumor), requiring high sensitivity assays. These assays have a number of limitations including low specificity, i.e., false positives. Another challenge with high sensitivity assays is identifying a "gold standard" wild-type population given that conventional tumor genotyping does have a chance of being falsely negative. Accordingly, there is a need in the art for high-sensitivity, high-specificity assays for the detection of molecular indicia of cancer.

SUMMARY OF THE INVENTION

The invention, relates in some aspects to the finding that cell free nucleic acids into body fluids by tumor cells have diagnostic and prognostic utility. The inventors of the present invention have generated a control platform that allows an accurate determination of whether a person carries the mutation of interest, or whether the result obtained is an artifact of the measuring assay. This platform is based on two concepts: (i) a quality control step and (ii) a 'gold standard' control population. According to one aspect of the invention, a method to monitor cell free DNA is provided. The method comprises obtaining a plasma sample from a subject known to have a cancer characterized by a pair of mutually exclusive mutations specific to the cancer; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; and indicating in a report that the subject has the first mutation when (a) the amount of the housekeeping gene and/or total DNA in the cell free nucleic acids isolated from the plasma sample is within the selected range and (b) the amount of the first mutation is increased as compared to a control amount, wherein the control amount is determined by measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject.

According to some aspects of the invention, a method to monitor cell free DNA is provided. The method comprises obtaining a plasma sample from a subject known to have a cancer characterized by a pair of mutually exclusive mutations specific to the cancer; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; and measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject. In some embodiments, the method further comprises indicating in a report that the subject has the first mutation when (a) the amount of the housekeeping gene and/or total DNA in the cell free nucleic acids isolated from the plasma sample is within the selected range and (b) the amount of the first mutation is increased as compared to a control amount.

In some embodiments, the amount of the first mutation is measured before and after administration of an anti-cancer therapy to the subject. In some embodiments, the sample collection, isolation and measuring steps are repeated so as to monitor the subject's amount of the first mutation over time. In some embodiments, a decrease in amount of the mutation indicates that the cancer is stabilizing or decreasing. In some embodiments, an increase in amount of the mutation indicates that the cancer is increasing. In some embodiments, the subject's amount of the first mutation is measured: (a) in a first sample obtained from the subject before the subject received an anti-cancer therapy; and (b) in a second sample obtained from the subject after the subject received an anti-cancer therapy.

According to some aspects of the invention, a method to treat cancer is provided. The method comprises obtaining a plasma sample from a subject known to have a cancer characterized by a pair of mutually exclusive mutations specific to the cancer; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject; and treating the subject with an anti-cancer therapy when (a) the amount of the housekeeping gene and/or total DNA in the cell free nucleic acids isolated from the plasma sample is within the selected range and (b) the amount of the first mutation is increased as compared to a control amount.

In some embodiments, the amount of the first mutation is measured before and after administration of the anti-cancer therapy to the subject. In some embodiments, the sample collection, isolation and measuring steps are repeated so as to monitor the subject's amount of the first mutation over time. In some embodiments, administration of the anti-cancer therapy is maintained when the amount of the mutation decreases over time. In some embodiments, the anti-cancer therapy is administered at a higher dosage or is changed when the amount of the mutation increases over time. In some embodiments, the subject's amount of the first mutation is measured: (a) in a first sample obtained from the subject before the subject received the anti-cancer therapy; and (b) in a second sample obtained from the subject after the subject received the anti-cancer therapy.

According to some aspects of the invention, a method to monitor efficacy of an anti-cancer therapy is provided. The method comprises administering an anti-cancer therapy to a subject known to have a cancer characterized by a pair of mutually exclusive mutations specific to the cancer; obtaining a plasma sample from the subject; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; and measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject.

In some embodiments, the amount of the first mutation is measured before and after administration of the anti-cancer therapy to the subject. In some embodiments, the sample collection, isolation and measuring steps are repeated so as to monitor the subject's amount of the first mutation over time. In some embodiments, the anti-cancer therapy is efficacious when the amount of the mutation decreases over time. In some embodiments, the anti-cancer therapy is not efficacious when the amount of the mutation increases over time. In some embodiments, the subject's amount of the first mutation is measured: (a) in a first sample obtained from the subject before the subject received the anti-cancer therapy; and (b) in a second sample obtained from the subject after the subject received the anti-cancer therapy.

The following embodiments apply equally to the various aspects of the invention set forth herein unless indicated otherwise.

In some embodiments, the measuring of: (a) the first of the pair of mutually exclusive mutations specific to the cancer in the cell free nucleic acids isolated from the plasma sample obtained from the subject and (b) the apparent amount of the first mutation in cell free nucleic acids isolated from control plasma samples obtained from control subjects known to have the second of the pair of mutually exclusive mutations specific to the cancer is performed by quantitative PCR.

In some embodiments, the cancer is lung cancer. In some embodiments, the pair of mutually exclusive mutations comprises an epidermal growth factor receptor (EGFR) mutation and a Rat sarcoma (RAS) mutation. In some embodiments, the pair of mutually exclusive mutations comprises an epidermal growth factor receptor (EGFR) mutation and a v-Ki-ras2 Kirsten rat sarcoma viral oncogene homolog (KRAS) mutation. In some embodiments, the EGFR mutation is selected from the group consisting of: L858R, T790M, L861Q, G719S, del 19 and exon 20 insertions. In some embodiments, the KRAS mutation is G12C.

In some embodiments, the cancer is colon cancer. In some embodiments, the pair of mutually exclusive mutations comprises a v-raf murine sarcoma viral oncogene homolog B1 (BRAF) mutation and a Rat sarcoma (RAS) mutation. In some embodiments, the pair of mutually exclusive mutations comprises a v-raf murine sarcoma viral oncogene homolog B1 (BRAF) mutation and a v-Ki-ras2 Kirsten rat sarcoma viral oncogene homolog (KRAS) mutation. In some embodiments, the BRAF mutation is V600E.

In some embodiments, the cancer is a melanoma. In some embodiments, the pair of mutually exclusive mutations comprises a v-raf murine sarcoma viral oncogene homolog B1 (BRAF) mutation and a Rat sarcoma (RAS) mutation. In some embodiments, the pair of mutually exclusive mutations comprises a v-raf murine sarcoma viral oncogene homolog B1 (BRAF) mutation and a neuroblastoma RAS viral (v-ras) oncogene homolog (NRAS) mutation.

In some embodiments, the amount of the first of the pair of mutually exclusive mutations specific to the cancer is measured by digital droplet PCR. In some embodiments, the amount of the first of the pair of mutually exclusive mutations specific to the cancer is determined by: preparing at least 2 serial dilutions of the cell free nucleic acids isolated from the plasma sample; measuring the amount of the first mutation in the at least 2 serial dilutions using digital droplet PCR; and evaluating linearity of the measured dilutions to confirm accuracy of the method.

In some embodiments, the measuring of: (a) the first of the pair of mutually exclusive mutations specific to the cancer in the cell free nucleic acids isolated from the plasma sample obtained from the subject and (b) the apparent amount of the first mutation in cell free nucleic acids isolated from control plasma samples obtained from control subjects known to have the second of the pair of mutually exclusive mutations specific to the cancer is performed by microarrays, Next-generation sequencing, chemiluminescence methods, fluorescent methods, digital detection, and mass spectrometry (MALDI-TOF).

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

(FIG. 10A demonstrates that a quantitative PCR for LINE-1 can quantify cfDNA concentration and is highly correlated with quantification using PicoGreen. Studying genotype concentration in gold standard positive cases, the false negative results all have either low or high levels of LINE-1 (FIG. 10 B). Sensitivity is 100% when cfDNA concentration is optimal, with a LINE-1 level between 3,000 and 650,000 pg/μL (dashed lines). Spheres represents EGFR-mutant cases and squares represents KRAS-mutant cases.

FIG. 13 shows ddPCR assay characteristics. As the sample input increases, the copies/μL output increases in a linear fashion across a wide dynamic range for both the L858R assay (FIG. 13A) and the exon 19 deletion assay (FIG. 13B). Testing for 10 and 50 copies of mutant EGFR in a background of 1000 and 50,000 genome equivalents (GE), the L858R assay demonstrates more consistent sensitivity (FIG. 13C) than the exon 19 deletion assay (FIG. 13D).

(FIG. 15A) Identical serial dilutions ranging from 10-10,000 T790M mutation copies per reaction were assayed in triplicates on three nonconsecutive days. Percent coefficients of variation ranged between 12.2-21.4% within days and 15.9-32.2% between days. (FIG. 15B) Technical replicates of samples containing either 1, 2, 10, or 20 copies of mutant T790M were assayed 32 times on the same day. Results show that ddPCR exhibits Poisson-distributed single molecule detection.

FIG. 16 shows EGFR mutation concentration in NSCLC patients.

DETAILED DESCRIPTION OF THE INVENTION

Figure 1:
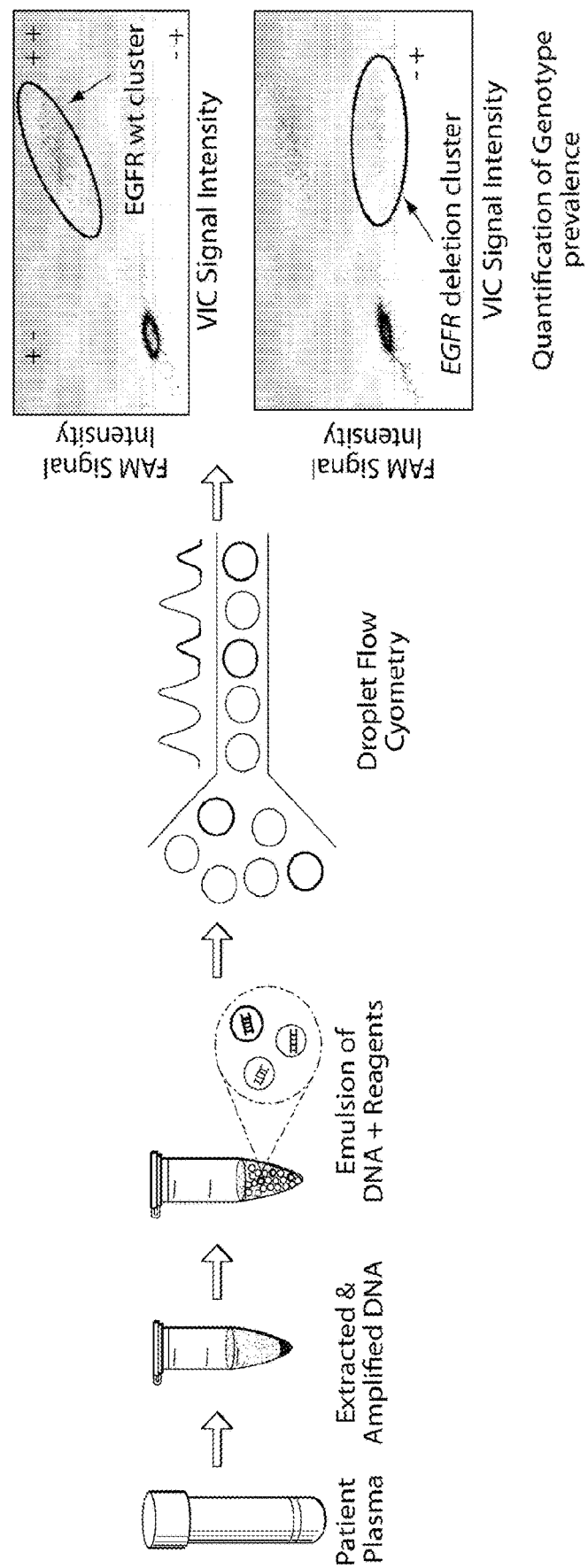
FIG. 1 shows the principle of digital droplet PCR as known in the prior art. Digital droplet PCR (ddPCR) takes advantage of recent developments in microfluids and surfactant chemistries. The reaction mixture is divided into approximately 20000 droplets which are PCR amplified, post-PCR fluorescently labeled and read in an automated droplet flow cytometer. Each droplet is assigned a positive and negative (1 or 0) value based on their fluorescent intensity. The amount of positives and negatives are read by flow cytometer and are used to calculate the concentration and the 95% Poisson confidence levels.

The present application relates to the analysis and monitoring of cell free DNA (cfDNA) for determining the physiological state of an organism, to monitor drug efficacy and dynamics, for early disease detection, as well as to ascertain molecular markers and fingerprints of identified molecules in such analysis to guide treatment. The methods of the invention provide non-invasive blood-based quantitative assays to perform disease diagnosis, monitoring, and pharmacodynamic assessment of drug efficacy. The present invention has a number of advantages not currently realized in clinical practice. First, the instant invention allows serial sampling of each subject, i.e., successive sampling of blood from the subject at different times. For example, samples can be collected from the subject at different times during therapy and/or before and after the subject has received any therapy. Second, the instant invention enables a direct match between a subject's tumor and therapeutic intervention, i.e, the choice of anti-cancer therapies is guided by the tumor genotype. Thirdly, it is broadly applicable across different cancer types. The assays described herein are highly-specific (i.e., allow for clinically actionable results by limiting false positives), quantitative (i.e., have potential to be used to monitor response to treatment) and are rapid (i.e., allow for a total turnaround time (TAT) of 1-3 days).

The present invention is based on the finding that tumor cells release cell free nucleic acids into body fluids, such as blood. This tumor-related cell free DNA has diagnostic and prognostic utility, and can be utilized for non-invasive tumor genotyping, thereby eliminating the need for repeat tumor biopsies. However, since these cell free nucleic acids are present in low amounts in body fluids, it is difficult to accurately detect genomic biomarkers in these nucleic acids as surrogates of tumor diagnosis and progression, leading to a high percentage of false positive and false negative results. In addition, procedures for isolating cell free DNA from a body fluid may cause loss of the cell free DNA and contamination by DNA released from cells present in the body fluid. This usually results in a longer processing time, a complicated processing method, a higher cost, and more importantly, lower sensitivity, specificity, and consistency.

The inventors of the present invention have addressed these problems by generating a control platform that allows an accurate determination of whether a person carries the mutation of interest, or whether the result obtained is an artifact of the measuring assay. This platform is based on two concepts: (i) a quality control step and (ii) a 'gold standard' control population. The quality control step identifies and utilizes a range of an amount of a housekeeping gene and/or total DNA to confirm that the isolated cell free nucleic acid is of sufficient quantity, quality and/or purity, thereby ensuring that the sensitivity of described methods. The 'gold standard' control population is subjects with a cancer having a mutation that does not exist in the test cancer population. This population as a gold standard control group takes into account two features. First, it recognizes that the blood of cancer subjects can be modified relative to normal populations, and therefore the control population is similar to the test population in that respect. Second, it takes advantage of the fact that many tumors exhibit mutually exclusive genetic mutations that are non-overlapping in cancer subjects. Thus, for any given pair of mutually exclusive mutations, there are test subjects who have (or are suspected to have) a first of the pair of mutations and "control subjects" that are known to have the second of the pair of mutually exclusive mutations, but who, in fact, should have zero amount of the first of the pair of mutually exclusive mutations (because the first and second mutations do not co-occur). It was discovered that these control subjects who only have the second mutation can have background activity in assays that read as though the first mutation also is present. The invention capitalizes on this by making those subjects the control subjects. These control subjects have a similar cancer and the 'apparent' amount of the first mutation measured in these control subjects represents the "normal range" or "control amount". The control amount is believed to be a very good measure of any artifacts or background interference in the measuring assays.

According to some aspects of the invention, methods to monitor cell free DNA (cfDNA) are provided. In some embodiments, the term "cfDNA" is used interchangeably with "circulating DNA" (ctDNA). The methods comprise obtaining a plasma sample from a subject known to have a cancer characterized by a pair of mutually exclusive mutations specific to the cancer; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; and indicating in a report that the subject has the first mutation when (a) the amount of the housekeeping gene and/or total DNA in the cell free nucleic acids isolated from the plasma sample is within the selected range and (b) the amount of the first mutation is increased as compared to a control amount, wherein the control amount is determined by measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject.

Cell free nucleic acids circulating in body fluids, such as extra-cellular DNA fragments and mRNAs, are molecular biomarkers for cancer. Unlike the uniformly truncated DNA released from apoptotic cells, DNA released from cancer cells due to necrosis, physical death, secretion, or disruption varies in size, and displays tumor related characteristics, such as decreased strand stability, oncogene and tumor suppressor gene mutations, microsatellite alterations, and gene hypermethylation. The detection of cancer-related mutations in the cell free nucleic acids is clinically useful for the diagnosis and management of cancer.

As used herein, "a pair of mutually exclusive mutations specific to the cancer" means a pair of mutations that are non-overlapping in cancer subjects. Many tumor profiling projects have observed mutually exclusive genomic alterations across many patients—for example, EGFR and KRAS are mutated in lung cancer, but no patients harbor both genetic lesions. Additional non-limiting examples in other cancer types include mutual exclusivity between BRAF and KRAS mutations (both involved in the common RAS/RAF signaling pathway) in colon cancer; BRAF and NRAS mutations in melanoma; APC and CTNNB1 mutations (both involved in the beta-catenin signaling pathway) in colorectal cancer, TP53 mutations and MDM2 copy number amplification in glioblastomas and mutual exclusivity between BRCA1/2 mutations and BRCA1 epigenetic silencing in serous ovarian cancer (The Cancer Genome Atlas Research Network 2011; Ciriello et al, Genome Research 2011; The Cancer Genome Atlas Research Network 2008). Other examples of mutually exclusive mutations are described in Cui Q, PLoS One. 2010).

A cancer characterized by a pair of mutually exclusive mutations specific to the cancer is a cancer that has a pair of mutually exclusive mutations. In some embodiments, these mutations are "passenger" mutations, i.e., they are functionally neutral and do not contribute to tumor development. In preferred embodiments, these mutations are "driver" mutations, i.e., they contribute to the tumorigenesis. Non-limiting examples of cancer include lung cancer, colon cancer, melanoma, ovarian cancer, breast cancer, glioblastomas, thyroid cancer, and prostate cancer.

In some embodiments, the cancer is lung cancer, and the pair of mutually exclusive mutations comprises an epidermal growth factor receptor (EGFR) mutation and a v-Ki-ras2 Kirsten rat sarcoma viral oncogene homolog (KRAS) mutation. In some embodiments, the EGFR mutation is selected from the group consisting of: leucine (L) to an arginine (R) substitution at position 858 (L858R), threonine (T) to a methionine (M) substitution at position 790 (T790M), leucine (L) to a glutamine (Q) substitution at position 861 (L861Q), glycine (G) to a serine (S) substitution at position 719 (G719S), exon 19 deletions (del 19) and exon 20 insertions. In some embodiments, the KRAS mutation is glycine (G) to a cysteine (C) substitution at position 12 (G12C).

In some embodiments, the cancer is colon cancer, and the pair of mutually exclusive mutations comprises a v-raf murine sarcoma viral oncogene homolog B1 (BRAF) mutation and a v-Ki-ras2 Kirsten rat sarcoma viral oncogene homolog (KRAS) mutation. In some embodiments, the BRAF mutation is a valine (V) to a glutamic acid (E) substitution at position 600 (V600E).

In some embodiments, the cancer is a melanoma, and the pair of mutually exclusive mutations comprises a v-raf murine sarcoma viral oncogene homolog B1 (BRAF) mutation and a neuroblastoma RAS viral (v-ras) oncogene homolog (NRAS) mutation.

"Subject" as used herein, refers to a human or animal, including all vertebrates, e.g., mammals such as primates (particularly higher primates), sheep, dog, rodents (e.g., mouse or rat), guinea pig, goat, pig, cat, rabbit, and cow, etc. Typically, the subject is a human, and is diagnosed with cancer using any suitable diagnostic method known in the art. For example a subject may be diagnosed with cancer using one or more of the following techniques: histopathology, imaging tests, and blood tests. Once the subject has been diagnosed with cancer, the type of cancer will determine whether the present invention can be used to monitor cell free nucleic acids. Thus, an additional determination is made whether the cancer characterized by a pair of mutually exclusive mutations specific to the cancer, i.e., whether the subject has a genetic mutation of a pair of mutually exclusive mutations specific to the cancer. The presence of the mutation can be determined using any suitable diagnostic method known in the art, for example, by tumor genotyping.

In some embodiments, any body fluid sample containing cell free DNA released by cancer cells can be used in the methods described herein. Examples of such body fluids include, without limitation, blood (serum/plasma), bone marrow (serum/plasma), cerebral spinal fluid, peritoneal fluid, pleural fluid, lymph fluid, ascites, serous fluid, sputum, lacrimal fluid, stool, urine, saliva, ductal fluid from breast, gastric juice, and pancreatic juice. In some embodiments, the sample used is blood. In preferred embodiments, the sample used is serum or plasma. In some preferred embodiments, the sample used is plasma. For cell free DNA in plasma, the concentration can range from 1-100 ng/ml in human samples.

Body fluids can be collected using any of the standard methods known in the art. Obtaining a plasma sample from a subject means taking possession of a plasma sample of the subject. In some embodiments, the plasma sample may be removed from the subject by a medical practitioner (e.g., a doctor, nurse, or a clinical laboratory practitioner), and then provided to the person performing the measuring steps of the assay described herein. The plasma sample may be provided to the person performing the measuring steps by the subject or by a medical practitioner (e.g., a doctor, nurse, or a clinical laboratory practitioner). In some embodiments, the person performing the measuring steps obtains a plasma sample from the subject by removing a blood sample from the subject and isolating plasma from the blood sample.

Cell free DNA from a biological/plasma sample can be isolated from the bodily fluid/plasma samples using any method known in the art. For example, the potentially contaminating cells can be removed from a body fluid by centrifugation and/or filtration. The proteins that may interfere with the detection of the cell free DNA can be removed, e.g., by proteinase K digestion. The cell free DNA may be further purified after removal of the cells and proteins from the body fluid, using any of the methods known in the art.

For example, the cell free DNA may be extracted with phenol, precipitated in alcohol, and dissolved in an aqueous solution.

Isolation of cell free DNA from a body fluid may cause loss of the DNA and contamination by DNA released from cells present in the body fluid. This usually results in a longer processing time, a complicated processing method, a higher cost, and lower sensitivity, specificity, and consistency. The inventors of the present invention have developed a quality control platform to optimize the calling criteria of the cell free tumor DNA assay described herein. Thus, as a quality control step, the methods described herein utilize the amount of a housekeeping gene and/or total DNA to confirm that the isolated cell free nucleic acid is of sufficient quantity, quality and/or purity so as to ensure that the sensitivity of described methods is accurate. Housekeeping genes are typically constitutive genes that are required for the maintenance of basic cellular function, and are expressed in all cells of an organism under normal and pathophysiological conditions. Non-limiting examples of housekeeping genes include Line1, GAPDH, HSP90, β-actin, and β-2-microglobulin. Samples are assayed for quality by measuring the amount of a housekeeping gene and/or total DNA in the cell free nucleic acids isolated from the plasma sample, and confirming that the amount of the housekeeping gene and/or total DNA in the sample is within a selected range. An amount of the housekeeping gene and/or total DNA higher than the selected range indicates suboptimal sample preparation and blood lysis which impacts DNA quantity, quality and/or purity. An amount lower than the selected range is indicative of too little input material. One of ordinary skill in the art can determine the "selected range" using methods known in the art. In some embodiments, the housekeeping gene is Line1 and the selected range is between 100,000 pg/µl and 10 pg/µl. In some embodiments, the housekeeping gene is Line1, and the selected range is between 75,000 pg/µl and 25 pg/µl. In preferred embodiments, the housekeeping gene is Line1 and the selected range is between 50,000 pg/µl and 50 pg/µl. This quality control step can be performed before, after or simultaneously with the other measuring steps of the methods described herein.

The amount of the (i) housekeeping gene and/or total DNA, and (ii) the first mutation in the cell free nucleic acids isolated from the plasma sample can be determined using a number of methods well known in the art, e.g., quantitative PCR (qPCR), microarrays, Next-generation sequencing, or gel electrophoresis based, colorimetric detection assays such as chemiluminescence methods, fluorescent methods, digital detection, and mass spectrometry (e.g., MALDI-TOF). In a preferred embodiment, qPCR is employed since it allows routine and reliable quantification of PCR products. In some preferred embodiments, digital droplet PCR is used to determine the amount of the (i) housekeeping gene and/or total DNA, and (ii) the first mutation in the cell free nucleic acids isolated from the plasma sample. The fundamental advantages that digital droplet PCR (ddPCR) offers are (a) an increase in dynamic range, (b) improvement in precision of detecting small changes in template DNA, (c) its ability to tolerate a wide range of amplification efficiencies, and (d) its ability to measure absolute DNA concentrations.

A "control amount" is determined by measuring the apparent amount of the first mutation in control cell free nucleic acids isolated from plasma samples obtained from control subjects known to have the second of the pair of mutually exclusive mutations specific to the cancer. The control amount is measured under conditions that are substantially the same as those used to measure the amount of the first mutation in the cell free nucleic acids isolated from the plasma sample from the subject. Since the pair of mutually exclusive mutations are non-overlapping in cancer subjects, the amount of the first mutation in control cell free nucleic acids obtained from control subjects known to have the second of the pair of mutually exclusive mutations specific to the cancer is expected to be zero (because the first and second mutations do not co-occur). However, the quantification assay and the measuring conditions used may lead to the detection of an apparent or superficial amount of the first mutation in subjects known to have the second mutation. Thus, these control subjects who only have the second mutation can have background activity in assays that read as though the first mutation also is present. These control subjects have a similar cancer and the 'apparent' amount of the first mutation measured in these control subjects represents the "normal range" or "control amount". The control amount is believed to be a very good measure of any artifacts or background interference in the measuring assays. For example, the amount of EGFR mutation in cell free DNA in plasma samples from subjects with KRAS-mutant non-small cell lung cancer is expected to be zero, since EGFR mutations and the KRAS mutations are non-overlapping in lung cancer. However, presence of the EGFR mutation was detected in a very low amount in subjects with KRAS-mutant lung cancer, indicating that this is the "normal range" for specificity (FIG. 2), which represents an artifact or background interference in the measuring assay. In some embodiments, the control amount for the L858R and del 19 mutations from KRAS mutant cancer is 0-10 and 0-1 copies/ml.

A tangible or electronic report indicating the results of the analysis, i.e. the subject has the first mutation when (a) the amount of the housekeeping gene and/or total DNA in the cell free nucleic acids isolated from the plasma sample is within the selected range and (b) the amount of the first mutation is increased as compared to a control amount, and any other information pertaining to the analysis could optionally be generated as part of the analysis (which may be interchangeably referred to herein as "providing" a report, "producing" a report, or "generating" a report). Examples of reports may include, but are not limited to, reports in paper (such as computer-generated printouts of test results) or equivalent formats and reports stored on computer readable medium (such as a CD, computer hard drive, or computer network server, etc.). Reports, particularly those stored on computer readable medium, can be part of a database (such as a database of patient records, which may be a "secure database" that has security features that limit access to the report, such as to allow only the patient and the patient's medical practitioners to view the report, for example).

A report can further be transmitted, communicated or reported (these terms may be used herein interchangeably), such as to the subject who was tested, a medical practitioner (e.g., a doctor, nurse, clinical laboratory practitioner, genetic counselor, etc.), a healthcare organization, a clinical laboratory, and/or any other party intended to view or possess the report. The act of 'transmitting' or 'communicating' a report can be by any means known in the art, based on the form of the report, and includes both oral and non-oral transmission. Furthermore, "transmitting" or "communicating" a report can include delivering a report ("pushing") and/or retrieving ("pulling") a report. For example, reports can be transmitted/communicated by such means as being physically transferred between parties (such as for reports in paper format), such as by being physically delivered from one party to another, or by being transmitted electronically or in signal form (e.g., via e-mail or over the internet, by facsimile, and/or by any wired or wireless communication methods known in the art), such as by being retrieved from a database stored on a computer network server, etc.

In some embodiments, the amount of the (i) housekeeping gene and/or total DNA, and (ii) the first of the pair of mutually exclusive mutations specific to the cancer is determined by preparing at least 2 serial dilutions of the cell free nucleic acids isolated from the plasma sample; measuring the amount of the (i) housekeeping gene and/or total DNA, and (ii) the first mutation in the at least 2 serial dilutions using digital droplet PCR; and evaluating linearity of the measured dilutions to confirm accuracy of the method. Linearity of dilution refers to the ability of the analytical method, within the assay range to obtain test results that are close to the expected amount of the mutation in the diluted sample. Linearity is measured by the r-squared ($r^2$ coefficient of determination, or r, coefficient of correlation) value for the linear regression of the expected versus observed concentration.

In some embodiments, the amount of the first mutation is measured before and after administration of a an anti-cancer therapy to the subject. As used herein, "anti-cancer therapy" refers to any therapy that has as a goal to reduce the severity of a cancer or to at least partially eliminate a cancer. Alternatively, "anti-cancer therapy" refers to any therapy that has as a goal to reduce or to at least partially eliminate metastasis of a cancer. Anti-cancer therapy includes chemotherapy, radiation, surgery, and some combination of these and other therapeutic options. In some embodiments, therapy targeted to the first of the pair of mutually exclusive mutations specific to the cancer is administered to the subject.

In some embodiments, the amount of the housekeeping gene and/or total DNA in the cell free nucleic acids isolated from the plasma sample and (b) the amount of the first mutation is measured repeatedly so as to monitor the subject's amount of the first mutation over time. In some embodiments, the amount of the first mutation is measured in a first sample that is obtained from the subject before the subject has received any anti-cancer therapy, and in a second sample that is obtained from the subject after the subject has received an anti-cancer therapy. In some embodiments, a decrease in amount of the first mutation over time indicates that the cancer is stabilizing or decreasing. In some embodiments, an increase in amount of the first mutation over time indicates that the cancer is increasing.

According to some aspects of the invention, a method to monitor efficacy of anti-cancer therapy is provided. The method comprises administering an anti-cancer therapy to a subject known to have a cancer characterized by a pair of mutually exclusive mutations specific to the cancer; obtaining a plasma sample from the subject; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; and measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject.

In some embodiments, the amount of the first mutation is measured before and after administration of the anti-cancer therapy to the subject. In some embodiments, the measuring steps are repeated so as to monitor the subject's amount of the first mutation over time. The anti-cancer therapy is considered to be efficacious, i.e., successful in producing the desired result, when the amount of the mutation decreases over time. The anti-cancer therapy is not efficacious, i.e., not successful in producing the desired result, when the amount of the mutation increases over time. In some embodiments, the subject's amount of the first mutation is measured: (a) in a first sample obtained from the subject before the subject received the anti-cancer therapy; and (b) in a second sample obtained from the subject after the subject received the anti-cancer therapy.

According to some aspects of the invention, a method to treat cancer is provided. The method comprises obtaining a plasma sample from a subject known to have a cancer characterized by a pair of mutually exclusive mutations specific to the cancer; isolating cell free nucleic acids from the plasma sample obtained from the subject; measuring the amount a housekeeping gene and/or total DNA in the cell free nucleic acids isolated from the plasma sample to confirm that the amount of housekeeping gene and/or total DNA in the sample is within a selected range; measuring the amount of a first of the pair of mutually exclusive mutations specific to the cancer in the cell free nucleic acids isolated from the plasma sample; measuring the apparent amount of the first mutation in control cell free nucleic acids isolated from plasma samples obtained from control subjects known to have the second of the pair of mutually exclusive mutations specific to the cancer using measuring conditions substantially the same as those used to measure the amount of the first mutation in the cell free nucleic acids isolated from the plasma sample from the subject; and treating the subject with an anti-cancer therapy when (a) the amount of the housekeeping gene and/or total DNA in the cell free nucleic acids isolated from the plasma sample is within the selected range and (b) the amount of the first mutation is increased as compared to a control amount.

The subject can be treated with an effective amount of any anti-cancer therapy. In some embodiments, the amount of the first mutation is measured before and after administration of the anti-cancer therapy to the subject. In some embodiments, the measuring steps are repeated so as to monitor the subject's amount of the first mutation over time. Administration of the anti-cancer therapy is maintained when the amount of the mutation decreases over time. Alternatively, the anti-cancer therapy is administered at a higher dosage or is changed when the amount of the mutation increases over time and/or a new mutation known to confer drug resistance (e.g., T790M) is measured.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1

Protocols for Sample Preparation and Droplet Digital PCR (ddPCR)

Plasma Isolation from Whole Blood
A. Equipment and Reagents
BD EDTA Tubes—Glass (BD #366450)
5-15 ml polypropylene tube
Pipettor—1000 µl,
RNase/DNase-free pipet tips (aerosol barrier)—1000 µl
15 ml polypropylene centrifuge tubes
Tabletop Centrifuge
B. Procedure
*To optimize DNA yield, about 10 ml of whole blood are required for each specimen.
**Plasma isolation should be carried out within one (1) hour of blood draw.
1. Remix the blood sample immediately prior to centrifugation.
2. Centrifuge the EDTA tubes at room temperature in a horizontal rotor (swing-out head) for 10 minutes at 1900 g (3000 rpm).
3. Without disturbing the whitish layer of mononuclear cells and platelets, aspirate the plasma using a micropipette and transfer to a 15 ml polypropylene conical tube.
4. Centrifuge the conical tube at 1900 g (3000 rpm) for 10 minutes at 40 C. Carefully transfer the plasma to a fresh 5-15 ml polypropylene tube, leave about 0.5 ml at the bottom of the tube undisturbed. About 4-5 ml of plasma can be obtained from 10 ml of whole blood sample. Polystylene tubes should not be used for this purpose. They will crack in −80° C. freezer.
5. Proceed to cfDNA extraction or immediately store the isolated plasma at −80° C. Thaw plasma samples at room temperature on the day of use.
Cell-Free DNA Extraction
A. Background
   Cell-free nucleic acids, such as tumor-specific extracellular DNA fragments and mRNAs in the blood or fetal nucleic acids in maternal blood, are present in serum or plasma usually as short fragments, <1000 bp (DNA) or <1000 nt (RNA). In addition, cell free miRNAs, as small as 20 nt, have the potential to provide biomarkers for certain cancers and disease states. The concentration of cell free nucleic acids in biological fluids such as plasma, serum, or urine, is usually low and varies considerably among different individuals. For cell free DNA in plasma, the concentration can range from 1-100 ng/ml in human samples. In samples obtained from different individuals, a similar sample-to-sample variability can be assumed for the concentration of cell free messenger RNA fragments and miRNA molecules.
B. Equipment and Reagents
Microfuge Centrifuge
SteriIGARD Hood
Water bath or heating block capable of holding 50 ml centrifuge tubes at 60° C.
Heating block or similar at 56° C. (capable of holding 2 ml collection tubes)
Daigger Vortex Genie 2
Pipettors—20 µl 200 µl, 1000 µl,
RNase/DNase-free pipet tips (aerosol barrier)—20 µl, 200 µl, 1000 µl
1.5 ml microcentrifuge tubes (Fisher #02-681-461)
50 ml centrifuge tubes
100% Ethanol
100% Isopropanol
Phosphate-buffered saline (PBS)
QIAamp Circulating Nucleic Acid Kit (Qiagen #55114)
Crushed Ice
C. Protocol
Before starting, make sure that buffers are prepared according to specifications in Qiagen QIAamp Circulating Nucleic Acids Kit manual. Wipe down lab bench, hood and pipetters with 70% ethanol.
Buffer ACB*
Before use, add 200 ml isopropanol (100%) to 300 ml buffer ACB concentrate to obtain 500 ml Buffer ACB. Mix well after adding isopropanol.
Buffer ACW1*
Before use, add 25 ml ethanol (96-100%) to 19 ml buffer ACW1 concentrate to obtain 44 ml
   Buffer ACW1. Mix well after adding ethanol.
Buffer ACW2†
Before use, add 30 ml ethanol (96-100%) to 13 ml buffer ACW2 concentrate to obtain 43 ml Buffer ACW2. Mix well after adding ethanol.
Adding carrier RNA to Buffer ACL*
Carrier RNA serves two purposes. Firstly, it enhances binding of nucleic acids to the QIAamp Mini membrane, especially if there are very few target molecules in the sample. Secondly, the addition of large amounts of carrier RNA reduces the chance of RNA degradation in the rare event that RNase molecules escape denaturation by the chaotropic salts and detergent in Buffer ACL.
Add 1550 µl Buffer AVE to the tube containing 310 µg lyophilized carrier RNA to obtain a solution of 0.2 µg/µl. Dissolve the carrier RNA thoroughly, divide it into conveniently sized aliquots, and store it at −15 to −30° C. Do not freeze-thaw the aliquots of carrier RNA more than three times.
Note that carrier RNA does not dissolve in Buffer ACL. It must first be dissolved in Buffer AVE and then added to Buffer ACL.
Calculate the volume of Buffer ACL-carrier RNA mix needed per batch of samples according to the tables in the kit manual. Select the number of samples to be simultaneously processed.
Gently mix by inverting the tube or bottle 10 times. To avoid foaming, do not vortex.
Protocol: Purification of cell free Nucleic Acids from 4 ml or 5 ml Serum or Plasma
For 1 ml, 2 ml, or 3 ml, see Qiagen kit manual, page 22.
Important Points Before Starting
All centrifugation steps are carried out at room temperature (15-25° C.).
Switch off vacuum between steps to ensure that a consistent, even vacuum is applied during protocol steps.
Things to do Before Starting
Equilibrate samples to room temperature.
If samples are <4 ml or <5 ml, bring the volumes up to 4 ml or 5 ml with phosphate-buffered saline.
Set up the QIAvac 24 Plus.
Heat a water bath or heating block to 60° C. for use with 50 ml centrifuge tubes in step 4.
Heat a heating block to 56° C. for use with 2 ml collection tubes in step 14.
Equilibrate Buffer AVE to room temperature for elution in step 15.
Ensure that Buffer ACB, Buffer ACW1, and Buffer ACW2 have been prepared.

Add carrier RNA reconstituted in Buffer AVE to Buffer ACL according to instructions in the table below.

TABLE 1

Volumes of Buffer ACL and carrier RNA (dissolved in Buffer AVE) required for processing ▲ 4 ml and ● 5 ml samples

| Number of samples | Buffer ACL (ml) ▲ | ● | Carrier RNA in Buffer AVE (μl) |
|---|---|---|---|
| 1 | 3.5 | 4.4 | 5.6 |
| 2 | 7.0 | 8.8 | 11.3 |
| 3 | 10.6 | 13.2 | 16.9 |
| 4 | 14.1 | 17.6 | 22.5 |
| 5 | 17.6 | 22.0 | 28.1 |
| 6 | 21.1 | 26.4 | 33.8 |
| 7 | 24.6 | 30.8 | 39.4 |
| 8 | 28.2 | 35.2 | 45.0 |
| 9 | 31.7 | 39.6 | 50.6 |
| 10 | 35.2 | 44.0 | 56.3 |
| 11 | 38.7 | 48.4 | 61.9 |
| 12 | 42.2 | 52.8 | 67.5 |
| 13 | 45.8 | 57.2 | 73.1 |
| 14 | 49.3 | 61.6 | 78.8 |
| 15 | 52.8 | 66.0 | 84.4 |
| 16 | 56.3 | 70.4 | 90.0 |
| 17 | 59.8 | 74.8 | 95.6 |
| 18 | 63.4 | 79.2 | 101.3 |
| 19 | 66.9 | 83.6 | 106.9 |
| 20 | 70.4 | 88.0 | 112.5 |
| 21 | 73.9 | 92.4 | 118.1 |
| 22 | 77.4 | 96.8 | 123.8 |
| 23 | 81.0 | 101.2 | 129.4 |
| 24 | 84.5 | 105.6 | 135.0 |

Procedure

1. Pipet 400 μl or 500 μl QIAGEN Proteinase K into a 50 ml centrifuge tube.
2. Add 4 ml or 5 ml of serum or plasma to the tube.
3. Add 3.2 ml or 4.0 ml Buffer ACL (containing 1.0 μg carrier RNA). Close the cap and mix by pulse-vortexing for 30 s.
Make sure that a visible vortex forms in the tube. To ensure efficient lysis, it is essential that the sample and Buffer ACL are mixed thoroughly to yield a homogeneous solution.
Note: Do not interrupt the procedure at this time. Proceed immediately to step 4 to start the lysis incubation.
4. Incubate at 60° C. for 30 min.
5. Place the tube back on the lab bench and unscrew the cap.
6. Add 7.2 ml or 9 ml Buffer ACB to the lysate in the tube. Close the cap and mix thoroughly by pulse-vortexing for 15-30 s.
7. Incubate the lysate—Buffer ACB mixture in the tube for 5 min on ice.
8. Insert the QIAamp Mini column into the VacConnector on the QIAvac 24 Plus. Insert a 20 ml tube extender into the open QIAamp Mini column.
Make sure that the tube extender is firmly inserted into the QIAamp Mini column in order to avoid leakage of sample.
Note: Keep the collection tube for the dry spin in step 13.
9. Carefully apply the lysate-Buffer ACB mixture from step 7 into the tube extender of the QIAamp Mini column. Switch on the vacuum pump. When all lysates have been drawn through the columns completely, switch off the vacuum pump and release the pressure to 0 mbar.
Carefully remove and discard the tube extender.
Please note that large sample lysate volumes (about 20 ml when starting with 5 ml sample) may need up to 15 minutes to pass through the QIAamp Mini membrane by vacuum force. For fast and convenient release of the vacuum pressure, the Vacuum Regulator should be used (part of the QIAvac Connecting System).

Note: To avoid cross-contamination, be careful not to move the tube extenders over neighboring QIAamp Mini Columns.
10. Apply 600 μl Buffer ACW1 to the QIAamp Mini column. Leave the lid of the column open, and switch on the vacuum pump. After all of Buffer ACW1 has been drawn through the QIAamp Mini column, switch off the vacuum pump and release the pressure to 0 mbar.
11. Apply 750 μl Buffer ACW2 to the QIAamp Mini column. Leave the lid of the column open, and switch on the vacuum pump After all of Buffer ACW2 has been drawn through the QIAamp Mini column, switch off the vacuum pump and release the pressure to 0 mbar.
12. Apply 750 of ethanol (96-100%) to the QIAamp Mini column. Leave the lid of the column open, and switch on the vacuum pump. After all of ethanol has been drawn through the spin column, switch off the vacuum pump and release the pressure to 0 mbar.
13. Close the lid of the QIAamp Mini column. Remove it from the vacuum manifold, and discard the VacConnector. Place the QIAamp Mini column in a clean 2 ml collection tube, and centrifuge at full speed (20,000×g; 14,000 rpm) for 3 min.
14. Place the QIAamp Mini Column into a new 2 ml collection tube. Open the lid, and incubate the assembly at 56° C. for 10 min to dry the membrane completely.
15. Place the QIAamp Mini column in a clean 1.5 ml elution tube (provided) and discard the 2 ml collection tube from step 14. Carefully apply 20-150 μl of Buffer AVE to the center of the QIAamp Mini membrane. Close the lid and incubate at room temperature for 3 min.
Important: Ensure that the elution buffer AVE is equilibrated to room temperature (15-25° C.). If elution is done in small volumes (<500) the elution buffer has to be dispensed onto the center of the membrane for complete elution of bound DNA. Elution volume is flexible and can be adapted according to the requirements of downstream applications. The recovered eluate volume will be up to 5 μl less than the elution volume applied to the QIAamp Mini column.
16. Centrifuge in a microcentrifuge at full speed (20,000×g; 14,000 rpm) for 1 min to elute the nucleic acids.
D. Storage—DNA shall be stored in 1.5 ml eppendorf tubes at 4° C. for immediate use. DNA shall be stored at −80° C. indefinitely.
E. Troubleshooting
  Little or no nucleic acids in the eluate
b) Extended time between blood draw and plasma preparation. Cells may disintegrate and release genomic DNA into the plasma, diluting the target nucleic acid.
e) Buffers not prepared correctly.
  General handling
Clogged QIAamp Mini column
Place the QIAamp Mini column in a 2 ml collection tube and spin it at full speed for 1 minute or until sample has completely passed through the membrane. Re-assemble the QIAamp Mini column with Tube Extender, VacConnector and (optional) VacValve. Transfer the remaining sample lysate into the Tube Extender, switch on the vacuum pump, open the VacValve, and pass the remaining lysate through the QIAamp Mini column. Repeat the above procedure if the QIAamp Mini column continues to clog.
Cryoprecipitates may have formed in plasma due to repeated freezing and thawing. These can block the QIAamp Mini column. Do not use plasma that has been frozen and thawed more than once. In case cryoprecipitates are visible clear the sample by centrifugation for 5 min at 16,000 g.

Droplet Digital PCR

A. Background

Figures 5, 7:
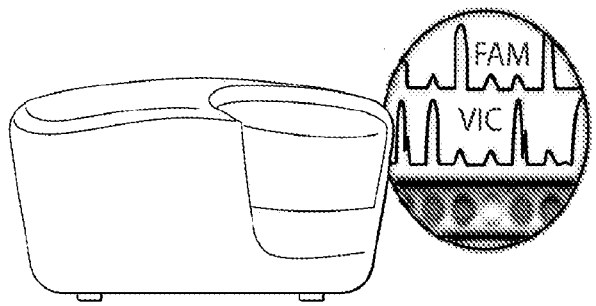
FIG. 7 shows the steps involved in digital droplet PCR.
Figures 6, 7:
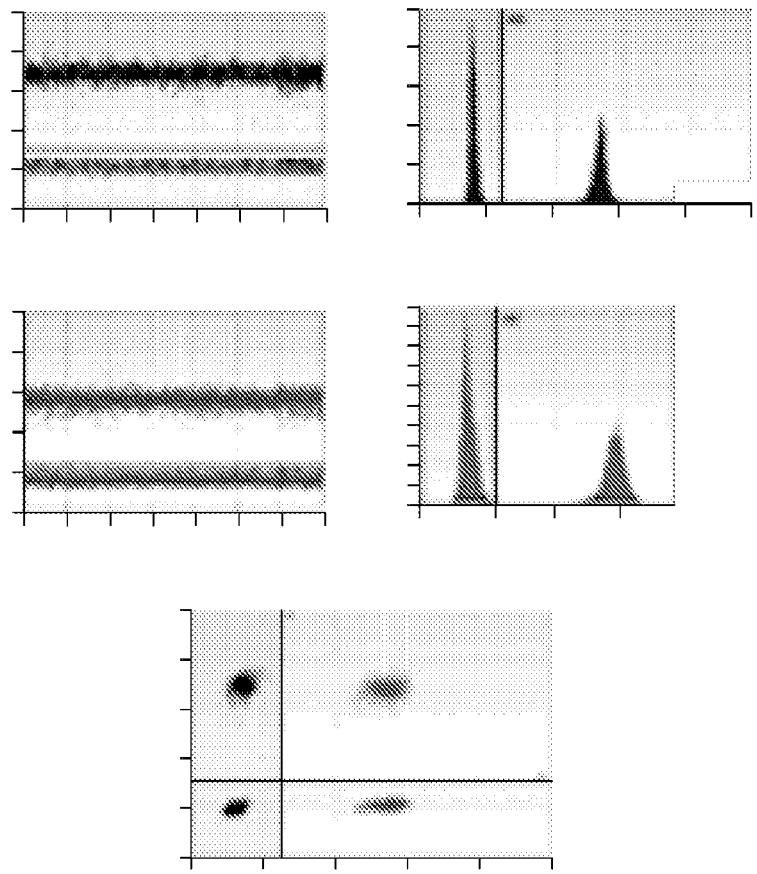

Droplet Digital™ PCR (ddPCR™) provides an absolute quantitation of target DNA molecules with accuracy, precision, and sensitivity. ddPCR applications include measurement of copy number variation, rare sequence detection, mutation detection, and gene expression analysis (FIG. 7).

B. Equipment and Reagents

Bio-Rad Tetra-Head or My-iQ thermal cycler
QX100 ddPCR system
Eppendorf PCR Plate Heat Sealer
Pipettors—2, 20, 200, 1000 ul
RNase/DNase-free pipet tips (aerosol barrier)—20 µl, 200 µl, 1000 µl
1.5 ml microcentrifuge tubes
Dnase-free. Rnase-free water
Twin Tec semi-skirted 96-well plates (Eppendorf #951020362)
Easy Pierce Foil PCR Plate Seals (Thermo-Fisher #AB-0757)
Droplet reader oil (Bio-Rad #1863004)
Droplet generation oil (Bio-Rad #1863005)
DG8 cartridge for ddPCR (Bio-Rad #1863008)
DG8 caskets for ddPCR (Bio-Rad #1863009)
2×ddPCR supermix for probes (Bio-Rad #1863010)
40× Taqman primer/probe mix (Life Technologies)

C. Precautions

As a general rule, set up the laboratory to avoid contamination:

Wipe down work surfaces using 70% ethanol: hood, bench, racks, pipettes, cartridge holders, waste beaker, droplet generator and heat sealer before you start and after you finish. Put UV (15 min timer) on when you are done in the hood (or ask another clean room user to do that for you when she finishes after you.) Clean the hood on weekly basis using DNA Zap.

Change gloves frequently: always use CLEAN gloves when prepare master mix, especially when open a Taqman probe tube. Change gloves between handling positive controls and patient samples.

Use aerosol resistant pipette tips and calibrated pipettes. Check liquid level in the tip before/after pipetting. Pipette into each reaction vessel once.

Have your own set of PCR reagents. Store the reagents (including water) in small aliquots.

D. Protocols i. Preparation of ddPCR Reactions:

*Remember to include a no template (water), wildtype and mutant control for every master mix.

1. When running multiple reactions, always make a master mix (with 10% extra volume) without the template. Add components in the following order, mix up and down several times by pipetting.

| Reagent | Final concentration |
|---|---|
| Water | * |
| 2xddPCR Supermix for Probes | 1x |
| 40xTaqman primer/probe mix | 1x |

2. Aliquot into the sample wells of the cartridges and add the DNA samples last. It is important to fill sample wells before filling oil wells (70 ul of Droplet Generation Oil) of the DG8 cartridges.

3. Cover the cartridges with a piece of DG8 gasket and load the cartridge into Droplet Generator.

4. When the light on Droplet Generator turns green, take out the cartridge.

5. Use a manual 50 ul 8-well channel pipette, gently pipette up 30 ul droplets while counting to five. Release the droplets into a 96-well PCR plate while counting to five.

6. Repeat droplet generation until all the cartridges are processed.

7. Cover the PCR plate with a sheet of Easy Pierce Foil PCR Plate Seal. Mark well A1 at the right corner. Seal the PCR plate with pre-heated Eppendorf PCR Plate Sealer: press down hard (second tier) and count six times. Flip the plate and press hard, count to six.

Remember to turn off the plate sealer after you are done.

8. Place the plate in a thermal cycler with pre-set ddPCR programs.

9. Select the appropriate program and start the PCR.

ii. Plate Reading on QX100 Reader:

1. Twenty minutes before the PCR program finishes, set up a new plate layout in QuantaSoft program.

2. Check and make sure the lights indicating levels of the QX100 reader oil and waste are green.

3. Prime the QX100 reader.

4. Transfer the finished PCR plate to the QX100 reader and begin reading.

5. Shut down the QX100 reader and instrument-attached laptop every Friday afternoon.

iii. ddPCR Cycling Conditions:

These programs were developed for Bio-Rad Tetra-Head and My-iQ cyclers. Other thermocyclers may require different profiles.

| Step | Temperature |
|---|---|
| 1 | 95 C. 10 min |
| | Ramp to 94 C. 2.5 C./sec |
| 2 | 94 C. 30 sec |
| | Ramp to annealing temp 2.5/sec |
| 3 | Annealing temp* 1 min |
| 2 and 3 | 40 cycles |
| 4 | 10 C. hold |

*See next section for annealing temperatures specific for each mutation detection assay.

iv. ddPCR Programs and Controls by Gene/Exon:

| Gene/Mutation | PCR program | Positive Controls |
|---|---|---|
| EGFR | | |
| Del 19 | ddPCR_55 | PC9 (del19) and A549 (EGFRwt) gDNA |
| L858R | ddPCR_58 | plasmids |
| T790M | ddPCR_58 | plasmids |
| KRAS | | |
| G12C | ddPCR_60 | plasmids |
| G12D | ddPCR_61 | plasmids |
| G12S | ddPCR_64 | A549 (G12S) and PC9 (KRASwt) gDNA |

Figures 1, 8:
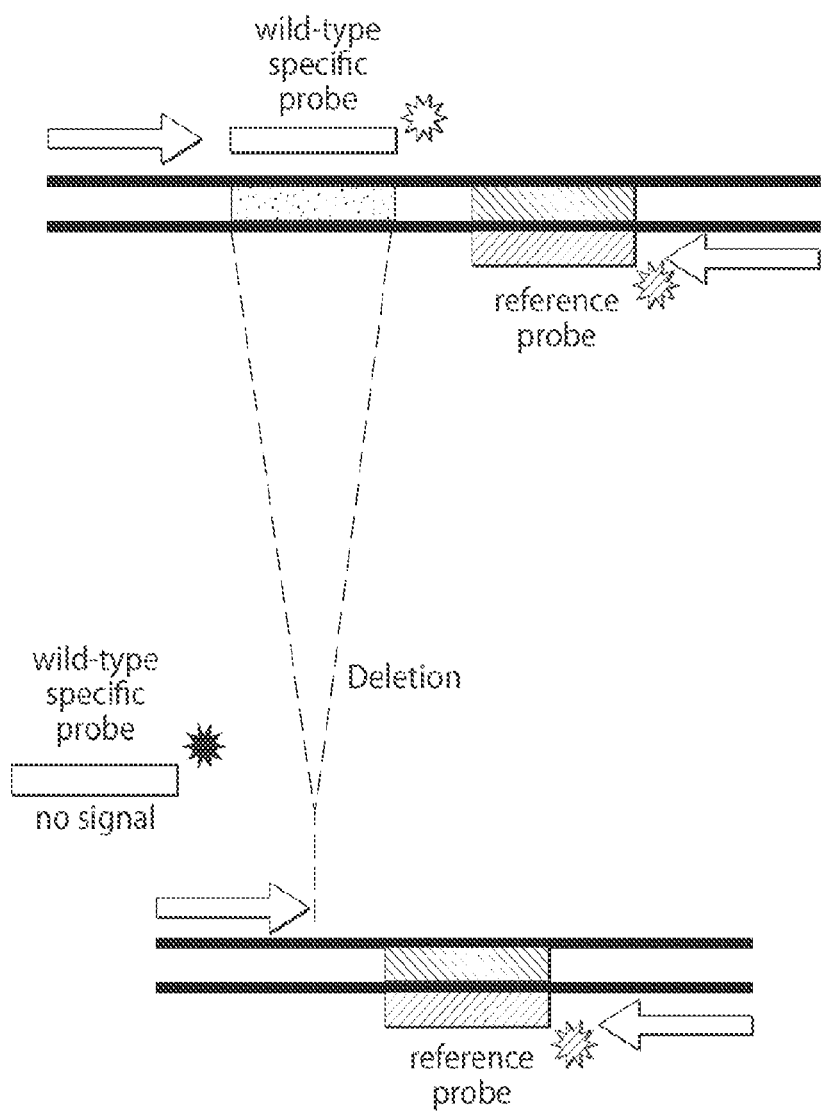
FIG. 8 shows the EGFR del19 ddPCR assay.
Figures 2, 8:
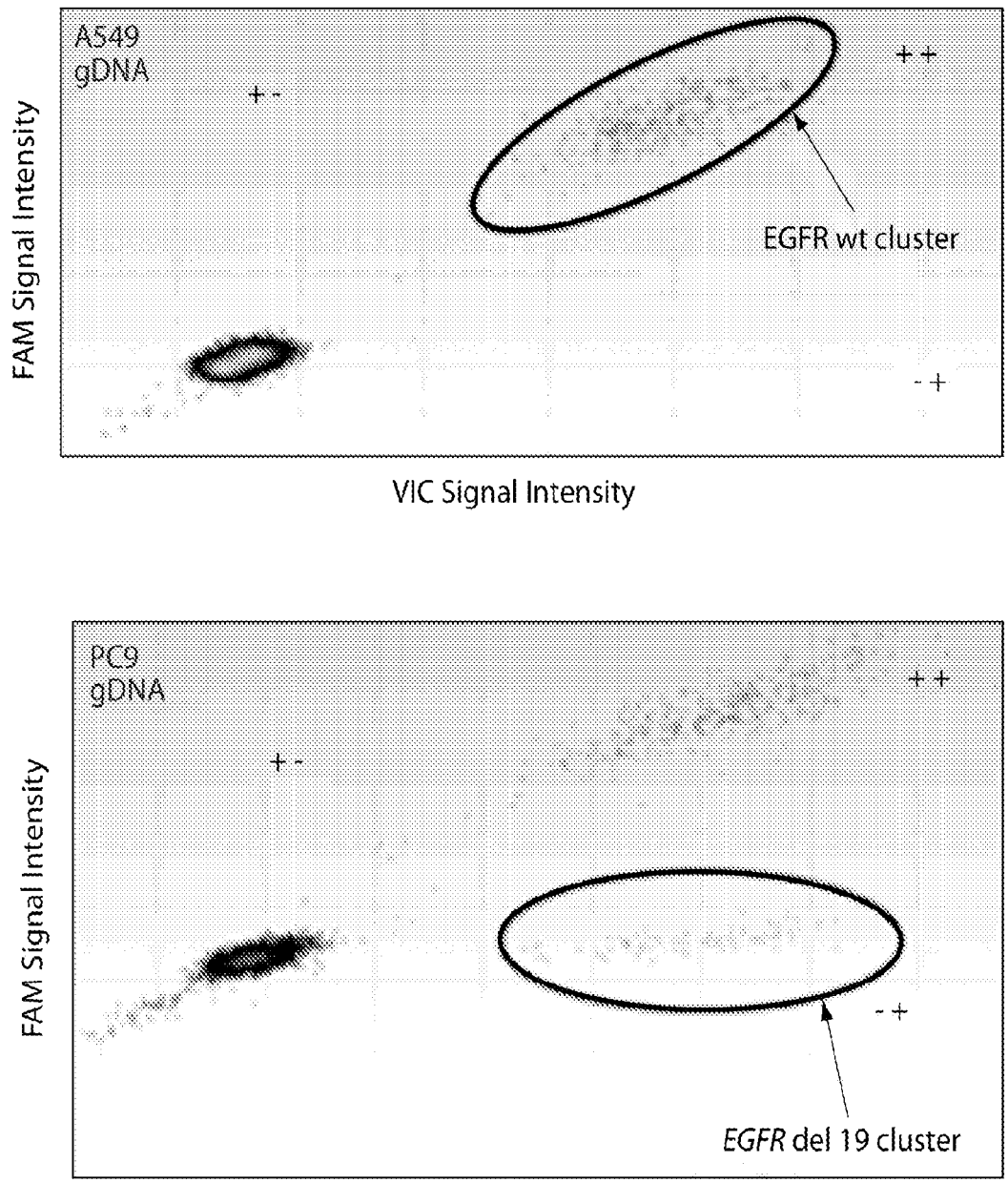

E. Custom Designed EGFR Del19 ddPCR Assay i. Assay Background:

Various exon 19 deletions are the most common EGFR activating mutations in NSCLC patients. This particular EGFR del 19 ddPCR assay is used to detect a deletion within exon 19 that causes a 4-5 amino acid deletion within the kinase domain of EGFR. Due to the short length of the exon (99 bp), the design of the primers extends to intronic sequences. Of the two primers, the forward primer lies in the exonic sequence, the reverse primer lies in the intronic sequence between exons 19 and 20. Of the two probes, the VIC-labeled "reference probe" sequence is shared by both the wildtype and the deletion mutants; the FAM-labeled probe sequence spans the hotspots of deletion area and is only present in EGFR ex19 wildtype samples. An EGFR ex19 wildtype sample will have both FAM- and VIC-labeled droplets, while an EGFR del19 mutant sample will only have VIC-labeled droplets (FIG. 8). The two populations can be easily grouped by free-hand function in QuantaSoft software.

```
Forward Primer:
                                         (SEQ ID NO: 1)
GTGAGAAAGTTAAAATTCCCGTC
39% GC 58.4° Tm Reverse Primer:
                                         (SEQ ID NO: 2)
CACACAGCAAAGCAGAAAC
47% GC 58.7° Tm Probe 1 (wildtype-specific)
                                         (SEQ ID NO: 3)
5'-FAM-AGGAATTAAGAGAAGCAACATC-MGB-3'
36% GC 72.2° Tm Probe 2 (reference)
                                         (SEQ ID NO: 4)
5'-VIC-ATCGAGGATTTCCTTGTTG-MGB-3'
42% GC 68.8° Tm
```

Results

Digital droplet PCR was used to develop a method of assessing tumor derived DNA from plasma samples of cancer patients. Digital droplet PCR (ddPCR) takes advantage of recent developments in microfluids and surfactant chemistries. The reaction mixture is divided into approximately 20000 droplets which are PCR amplified, post-PCR fluorescently labeled and read in an automated droplet flow cytometer. Each droplet is assigned a positive and negative (1 or 0) value based on their fluorescent intensity. The amount of positives and negatives are read by flow cytometer and are used to calculate the concentration and the 95% Poisson confidence levels (FIG. 1). The fundamental advantages that digital droplet PCR (ddPCR) offers are many, including (a) an increase in dynamic range, (b) improvement in precision of detecting small changes in template DNA, (c) its ability to tolerate a wide range of amplification efficiencies, and (d) its ability to measure absolute DNA concentrations.

Figure 2A:
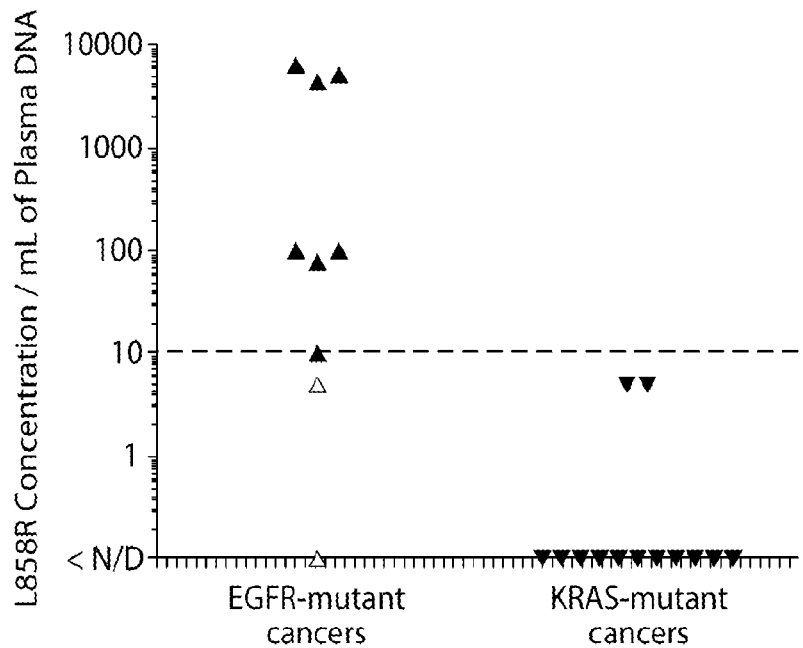
FIG. 2 shows the diagnostic accuracy of an embodiment of the assays described herein. EGFR mutations were tested in plasma from patients with KRAS-mutant NSCLC, genotype which is non-overlapping. The low concentrations of EGFR mutations we detected in this population can be considered the 'normal range" for analytical specificity (FIGS. 2A and B). Conversely, a KRAS G12C assay was developed and the same specificity test was performed (assaying for KRAS G12C mutation in EGFR and KRAS mutant patients' plasma) (FIG. 2C).
Figure 2B:
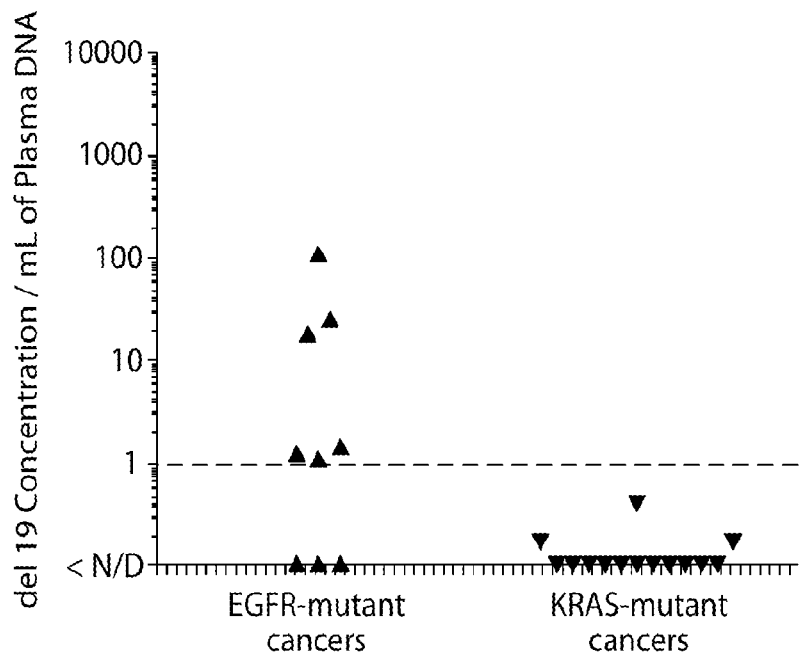
Figure 2C:
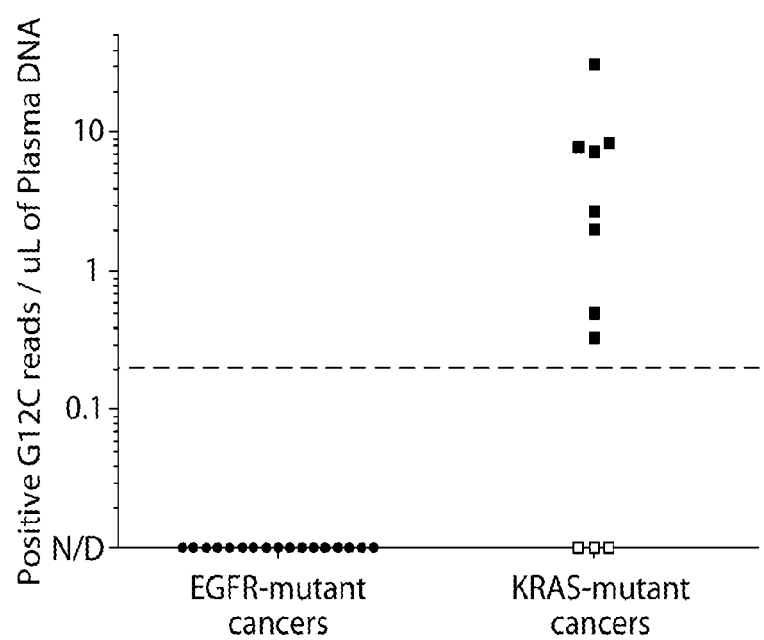

A particular challenge with high sensitivity assays is identifying a "gold standard" wild-type population given that conventional tumor genotyping does have a chance of being falsely negative, some wild-type cancers may actually carry the genotype of interest. To overcome this challenge, EGFR mutations were tested in plasma from patients with KRAS-mutant NSCLC, genotype which is non-overlapping. Thus, the low concentrations of EGFR mutations detected in this population can be considered the "normal range" for analytical specificity (FIGS. 2A and B). Conversely, a KRAS G12C assay was developed and the same specificity test was performed (assaying for KRAS G12C mutation in EGFR and KRAS mut patients' plasma) (FIG. 2C).

Figure 3A:
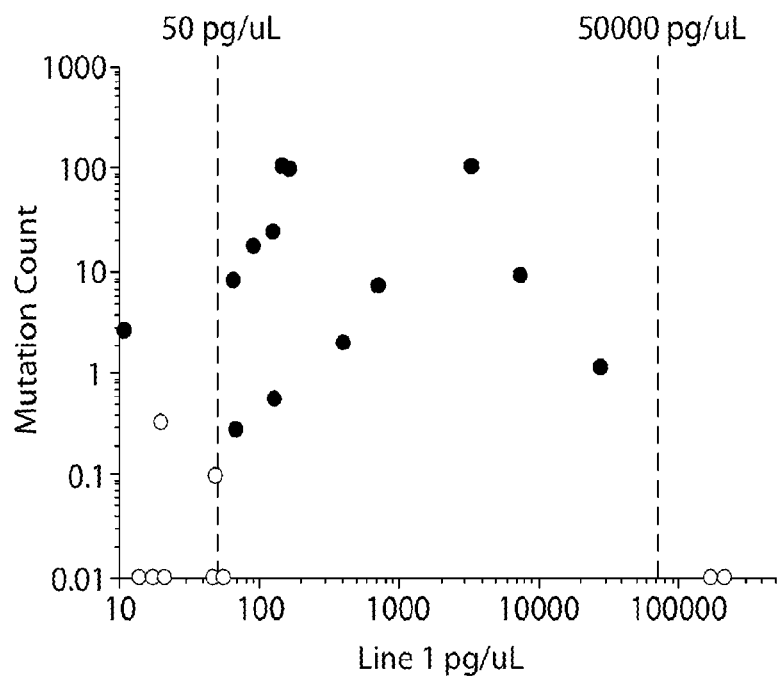
FIG. 3A demonstrates the quality control platform developed to optimize sensitivity of plasma DNA genotyping through monitoring factors that impact DNA quantity, quality, and purity. Samples are assayed for DNA quantity by measuring concentration of a housekeeper gene (Line1). Line-1 amount greater 50,000 pg/uL indicate sub optimal sample preparation and thereby impacting DNA quantity, quality, and purity. Line-1 amount below a certain threshold, in this case 50 pg/uL is indicative of too little input material.
Figure 3B:
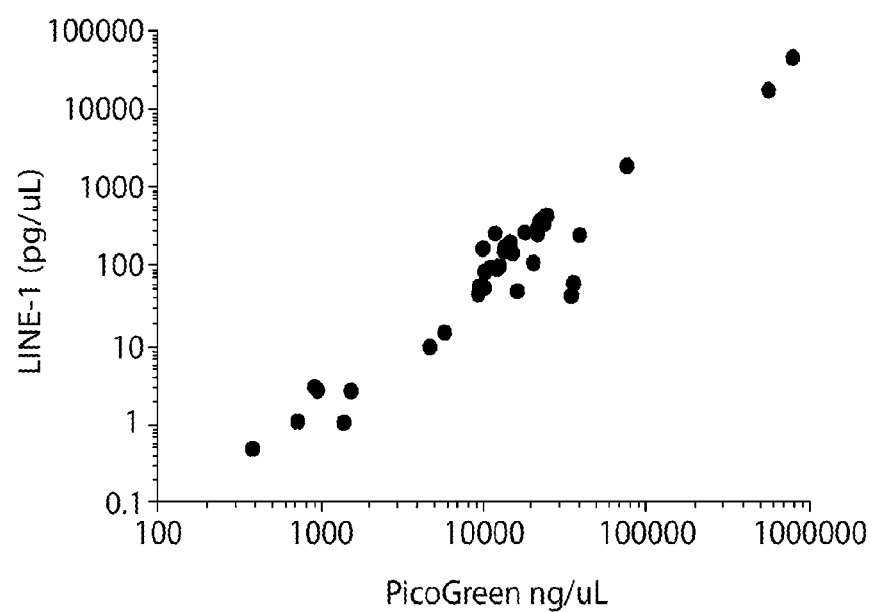
FIG. 3B shows that the Line-1 DNA amount correlates to total DNA amount in plasma.

A quality control platform was developed to optimize the calling criteria of our ctDNA assay (FIG. 3A). Samples are assayed for DNA quantity by measuring concentration of a housekeeper gene (Line1). Line-1 concentration greater than 50,000 pg/uL indicate sub optimal sample preparation and thereby impacting DNA quantity, quality, and purity. Line-1 concentrations below a certain threshold, in this case 50 pg/uL is indicative of too little input material. Line-1 DNA concentration correlates to total DNA concentration in plasma (FIG. 3B). Thus both Line-1 and/or total DNA concentration could be used for quality control.

Figure 4A:
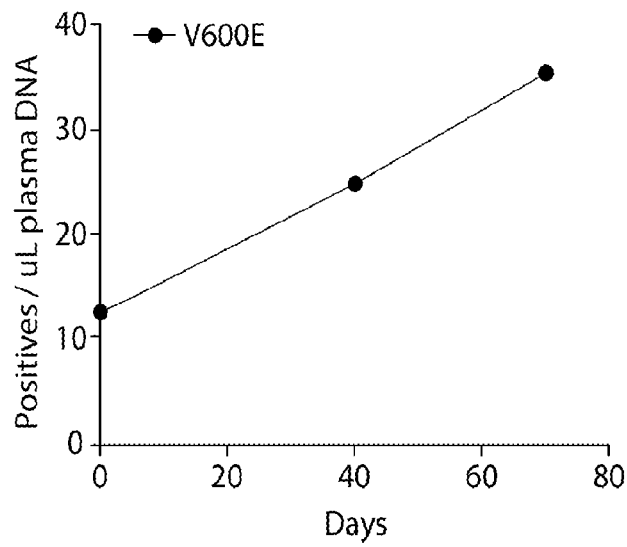
In FIG. 4A the patient received treatment, but continued to progress, whereas patient in example B received treatment and responded.
Figure 4B:
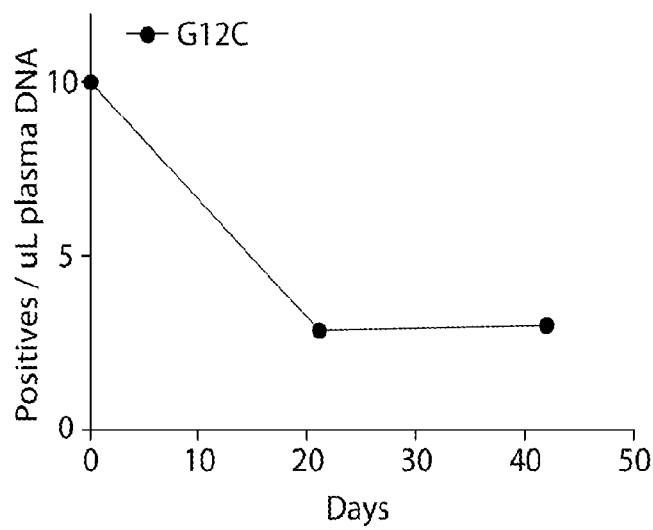
FIG. 4 shows preliminary data demonstrating that cfDNA genotyping allows non-invasive monitoring of response in lung cancer patients receiving therapy.

Preliminary data suggests that ctDNA genotyping allows non-invasive monitoring of response in lung cancer patients receiving therapy (FIG. 4). In FIG. 4A the patient received treatment, but continued to progress, whereas patient in FIG. 4B received treatment and responded.

Figure 5A:
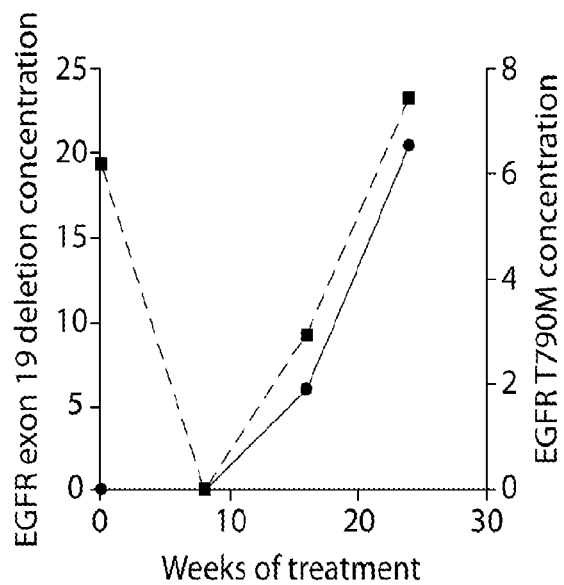
FIG. 5 demonstrates the monitoring evolution of resistance mutations, in this case EGFR T790M. Patients with EGFR-mutant lung cancer starting treatment with EGFR-targeted therapy underwent serial monitoring of EGFR exon 19 and EGFR T790M plasma genotype. Responding patients had normalization of their plasma genotype. When resistance developed, the original EGFR mutation again became detected (dashed line) as well as a new T790M resistance mutation (solid line). Genotyping of the patient's tumor at time of progression also demonstrated an acquired T790M resistance mutation. Intriguingly, plasma T790M was detected 8 weeks prior to clinical progression. These findings suggest serial cfDNA genotyping could allow monitoring for response as well as assessment for new mutations when resistance develops (FIG. 5A). The signal for acquired resistant (solid line in FIG. 5A) can be used to guide treatment with second generation therapies (demonstrated in FIG. 5B). In that case the resistance biomarker is used to change treatment and after treatment it becomes a marker to monitor whether the treatment works (similar to the dashed line in FIG. 5A).

Patients with EGFR-mutant lung cancer starting treatment with EGFR-targeted therapy underwent serial monitoring of EGFR exon 19 and EGFR T790M plasma genotype. Responding patients had normalization of their plasma genotype. When resistance developed, the original EGFR mutation again became detected (dashed line) as well as a new T790M resistance mutation (solid line). Genotyping of the patient's tumor at time of progression also demonstrated an acquired T790M resistance mutation. Intriguingly, plasma T790M was detected 8 weeks prior to clinical progression. These findings suggest serial ctDNA genotyping could allow monitoring for response as well as assessment for new mutations when resistance develops (FIG. 5A).

Figure 5B:
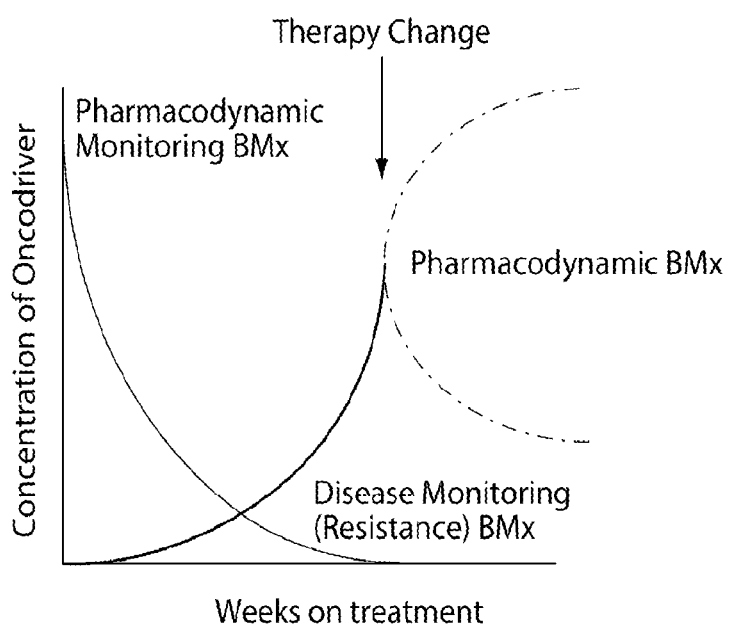
Figure 6:
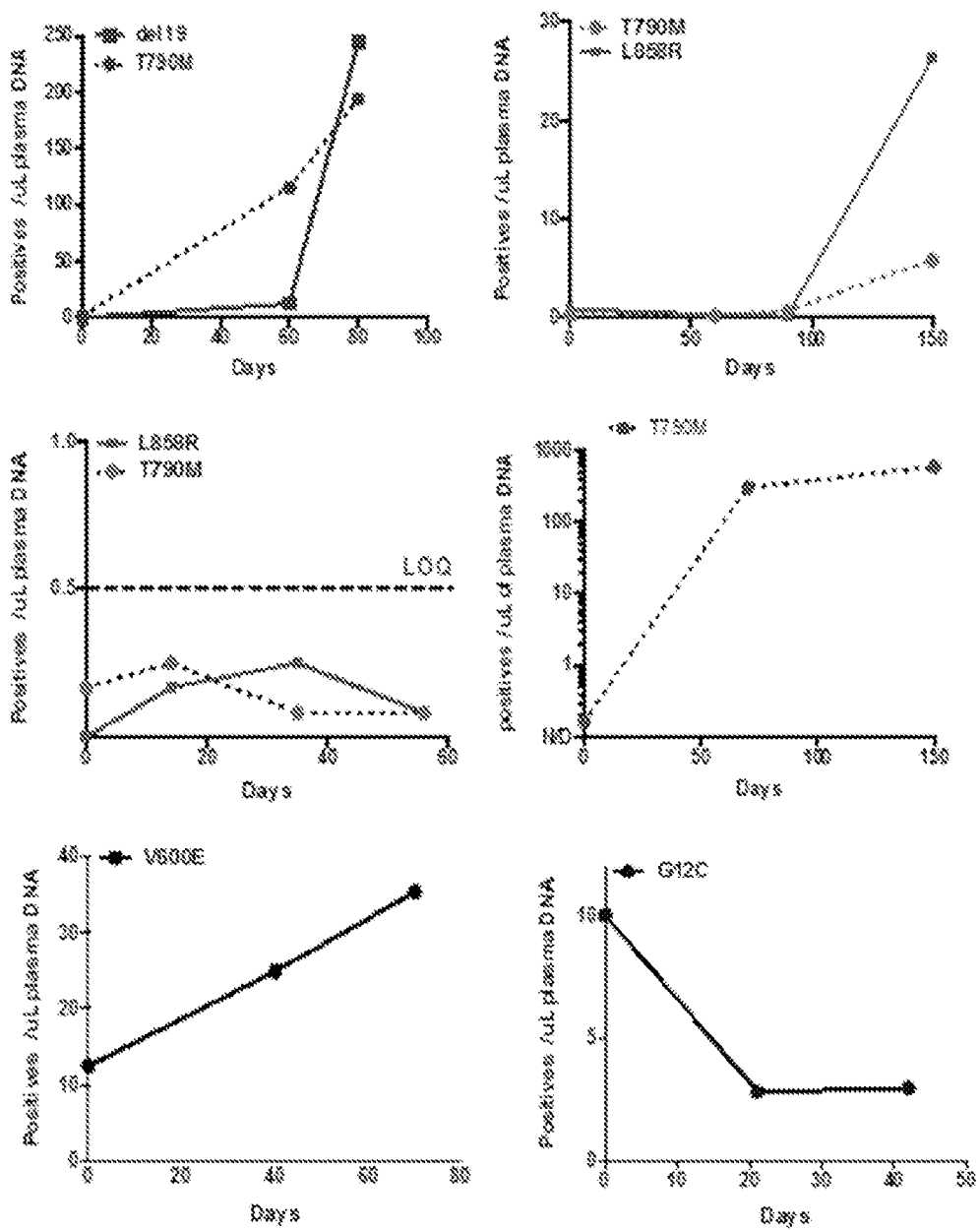
FIG. 6 shows more combinations of biomarkers.

The signal for acquired resistant (solid line in FIG. 5A) can be used to guide treatment with second generation therapies (demonstrated in FIG. 5B). In that case the resistance biomarker is used to change treatment and after treatment it becomes a marker to monitor whether the treatment works (similar to the dashed line in FIG. 5A). FIG. 6 shows more combinations of biomarkers.

REFERENCES

Ciriello et al., Mutual exclusivity analysis identifies oncogenic network modules. Genome Res. 2012. 22: 398-406

The Cancer Genome Atlas Research Network. 2008. Comprehensive genomic characterization defines human glioblastoma genes and core pathways. Nature 455: 1061-1068.

The Cancer Genome Atlas Research Network. 2011. Integrated genomic analyses of ovarian carcinoma. Nature 474: 609-615.

Cui Q, A network of cancer genes with co-occurring and anti-co-occurring mutations. PLoS One. 2010 Oct. 4; 5(10).

Example 2

Noninvasive Detection of Response and Resistance in EGFR-Mutant Lung Cancer Using Quantitative Next-Generation Genotyping of Cell-Free Plasma DNA Materials and Methods Patient Population For the primary study population, patients with advanced NSCLC undergoing routine tumor genotyping were selected. All patients consented to an IRB-approved protocol allowing collection and genomic analysis of blood specimens, limited to <50 mL of blood over any 3 month period. Patients were eligible for cfDNA analysis if they harbored a known EGFR or KRAS mutation in their NSCLC. Tumor genotyping of EGFR and KRAS was performed in a clinical, CLIA-approved laboratory. A second population of patients with advanced melanoma and a known BRAF genotype was also studied after consent to specimen collection on an IRB-approved protocol.

Plasma Collection

For each eligible patient, plasma was collected during routine care either prior to first-line therapy or at a subsequent time when the cancer was progressing on therapy. Additional follow-up specimens were collected if possible during routine care. Each specimen was collected into one 10 mL EDTA-containing vacutainer and was spun into plasma within 4 hours of collection. Plasma cfDNA was extracted and frozen at −80 C until genotyping. Total DNA concentration in extracted plasma was measured via a modified quantitative PCR assay for human long interspersed element 1 (LINE-1).

Droplet Digital PCR

Droplet Digital PCR (ddPCR) is a digital PCR technology that takes advantage of developments in microfluids and surfactant chemistries. Whereas conventional digital PCR involves a cumbersome process of diluting input DNA into individual wells for analysis, ddPCR emulsifies input DNA into ~20,000 droplets that are PCR amplified and fluorescently labeled, and then read in an automated droplet flow cytometer (FIG. 1). Each droplet is individually assigned a positive or negative value based on the fluorescent intensity. The amount of positives and negatives are read by a flow cytometer and are used to calculate the concentration of an allele. To minimize bias and to ensure the integrity of results, the laboratory was blinded to the tumor genotype when testing plasma specimens, but results were selectively unblinded for data analysis. Each plasma sample was analyzed in triplicate with an increasing quantity of input DNA (e.g. 1 µL, 2 µL, and 4 µL). Results were normalized to a mean concentration of mutant alleles per µL DNA input, and reported as copies of mutant allele per 100 µL of DNA, the approximate DNA quantity isolated from one blood specimen.

Results

Assay Characteristics

Two assays for EGFR L858R and exon 19 deletions were first developed; the latter assay was designed to detect loss of the wildtype signal and therefore could detect deletions of variable sequence. To demonstrate the analytical sensitivity and specificity of each assay, each ddPCR cycling condition was optimized to yield the maximum fluorescent signal with minimal increase in background signal. For each TaqMan probe, the optimal annealing temperature was determined by testing each assay across a temperature gradient of 55.0-65° C. Using serial dilutions of mutant DNA, it was found that ddPCR detects a mutation prevalence between 0.005% and 0.01% with a sensitivity of 5 to 50 mutant copies out of 10,000 (FIG. 13), depending on the mutation assayed. Experiments were repeated over three non-consecutive days. Both assays demonstrated linear quantification of allelic prevalence across a dynamic range spanning 4 orders of magnitude. From a technical standpoint, this suggested that ddPCR provides a reliable and quantitative measure of low prevalence EGFR mutant alleles within a plasma sample.

Maximizing Positive Predictive Value

To optimize the specificity of the EGFR genotyping assays (and utility in guiding clinical decisions), the incidence of false positive reads was tested in a gold-standard negative population. To ensure selection of patients certain to be wildtype for EGFR, patients with KRAS-mutant lung cancers were studied. Large studies have found that EGFR and KRAS mutations are non-overlapping in NSCLC and represent distinct cancer populations, therefore any EGFR-mutant DNA found in the plasma of patients with KRAS-mutant NSCLC can be interpreted as biologically insignificant and representative of the "normal range" for the assay.

Figure 9A:
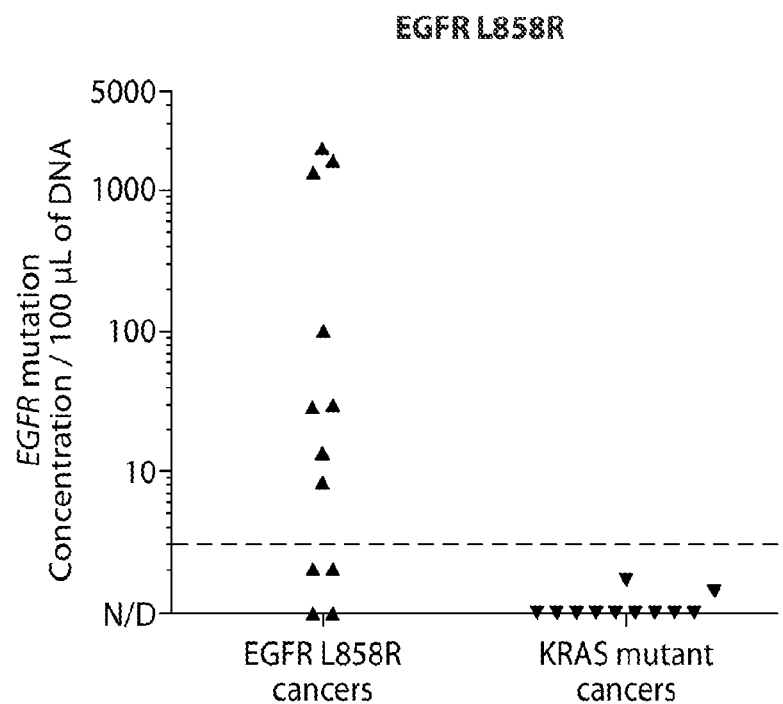
FIG. 9 demonstrates the detection of mutant alleles in gold standard positive and negative populations, using assays for EGFR L858R (FIG. 9A), EGFR exon 19 deletion (FIG. B), and KRAS G12C (FIG. C). Receiver operating curves are also shown (FIG. 9D, 9E, 9F). By studying plasma from lung cancer patients with a non-overlapping genotype, a normal range for the EGFR assays is identified to be 0-2 copies of L858R and 0-12 copies of exon 19 deletion per 100 μL of cfDNA. Setting the threshold for positive above this normal range, each assay has a sensitivity in the range of 66-79% with 100% specificity.
Figure 9B:
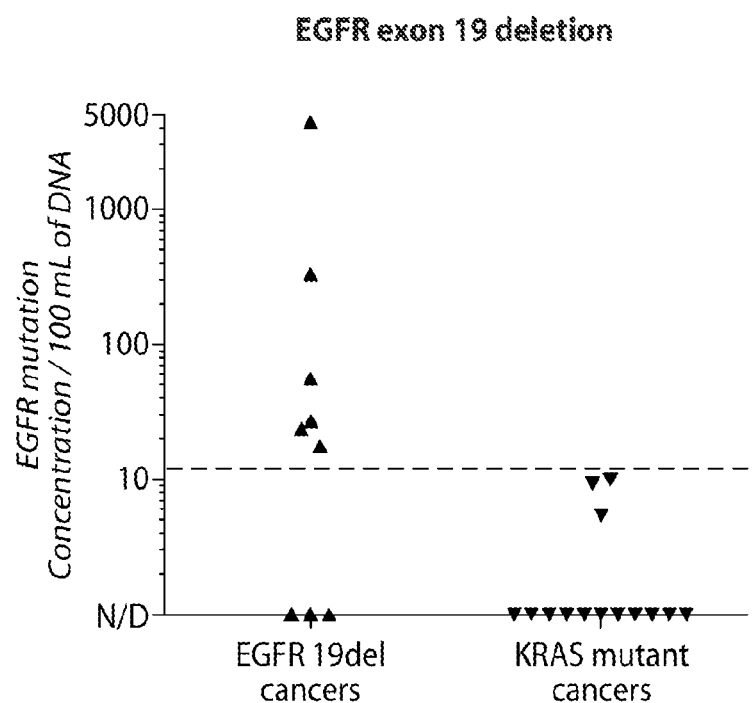
Figure 9C:
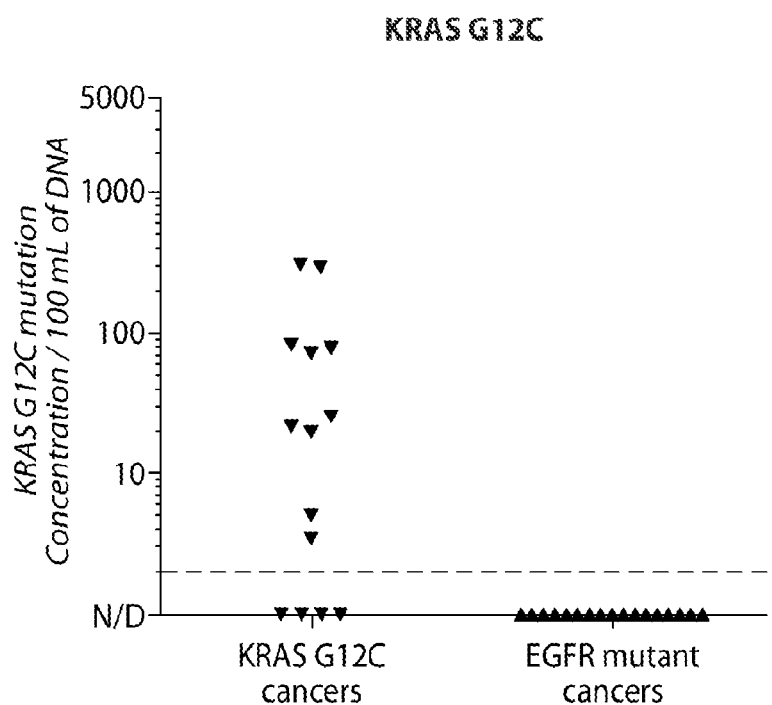
Figure 9D:
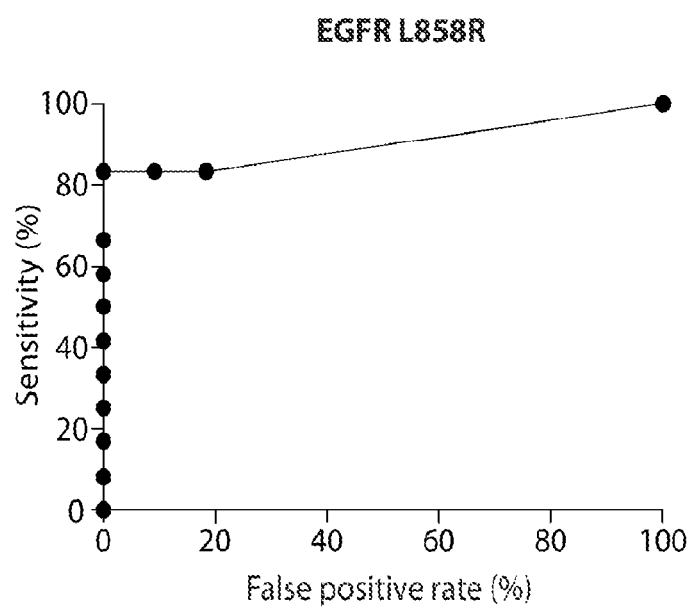
Figure 9E:
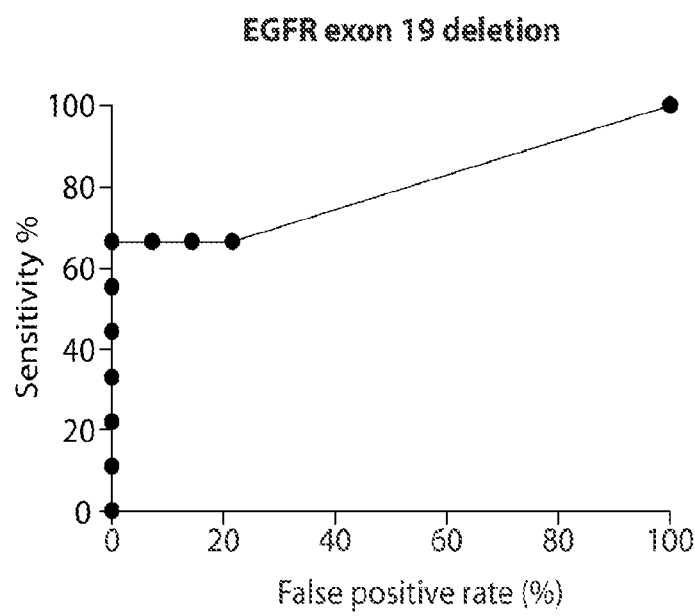
Figure 9F:
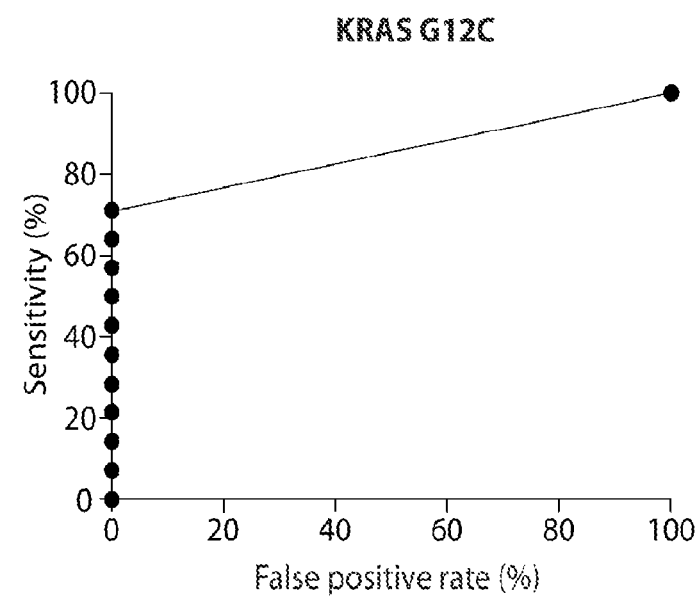

The EGFR L858R assay was first studied in 23 NSCLC patients, 12 with EGFR L858R and 11 with KRAS mutations in their cancers. Low levels of EGFR L858R were detected in 2 KRAS-mutant cases (18%) with a peak level of 1.7 mutations/100 µL of DNA (FIG. 9A). Using 2 mutations/100 µL of DNA as the threshold for a positive result, 8 of 12 cases were correctly identified as positive for EGFR L858R (66% sensitivity; 100% specificity). The variable exon 19 deletion assay was next studied in 23 NSCLC patients, 9 with EGFR exon 19 deletions and 14 with KRAS mutations in their cancers. Low levels of EGFR exon 19 deletions were detected in 3 KRAS-mutant cases (21%) with a peak value of 9.9 mutations/100 µL DNA (FIG. 9B). Using 12 mutations/100 µL of DNA as the threshold for a positive result, 6 of 9 cases were correctly identified as positive for EGFR exon 19 deletion (66% sensitivity; 100% specificity). Lastly, the reverse experiment was tested using a KRAS G12C assay that was developed as above. Of 17 patients with EGFR-mutant lung cancer, none had measurable mutant KRAS (FIG. 9C). Using a threshold of 1 mutation/100 µL of DNA, 11 of 14 KRAS G12C cases were correctly identified as positive (79% sensitivity; 100% specificity).

Figure 14:
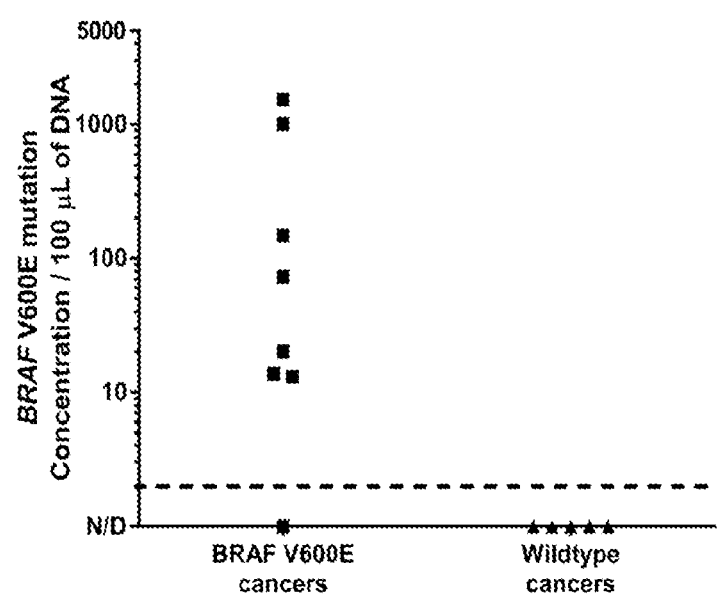
FIG. 14 demonstrates detection of BRAF V600E in cfDNA from patients with advanced melanoma. A threshold of 1 mutation/100 μL DNA results in 86% sensitivity and 100% specificity.

To gauge the generalizability of this assay to other genotype-defined malignancies, an assay was developed for BRAF V600E in the fashion described above and tested plasma specimens from 13 melanoma patients. Using a threshold of 1 mutation/100 µL of DNA for a positive result, we had a sensitivity of 86% and specificity of 100% (FIG. 14), demonstrating potential value of ddPCR genotyping in a disease other than NSCLC.

Quality Control to Improve Sensitivity

To better understand the false negative results in a subset of cases, LINE-1 was measured to assess the quantity and quality of cfDNA in each plasma specimen. LINE-1 is an easily measured, genomically common retrotransposon that has been previously used to estimate total DNA in plasma. The amplicons used for the LINE-1 qPCR assays are 82 bp and 107 bp, providing a snapshot of the minimum size of DNA fragments. LINE-1 levels were first measured in 69 specimens and compared them to overall DNA concentration as measured with PicoGreen (FIG. 10A) and found a high degree of correlation ($R^2$=0.94, p<0.0001). Median LINE-1 concentration was of 7700 pg/µL (interquartile range: 3072-14415 pg/µL) across 69 specimens.

Figure 10:
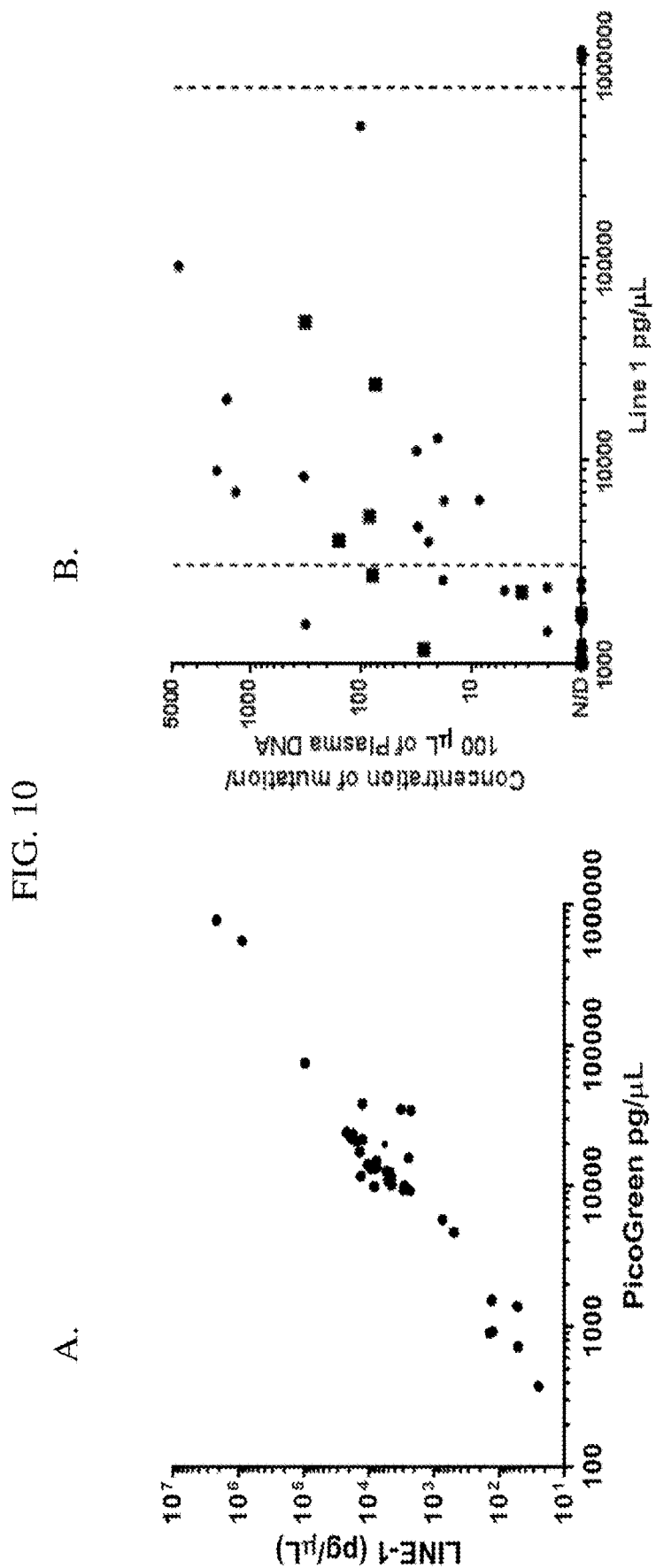
FIG. 10 shows plasma DNA quantification to optimize sensitivity.
Figure 11A:
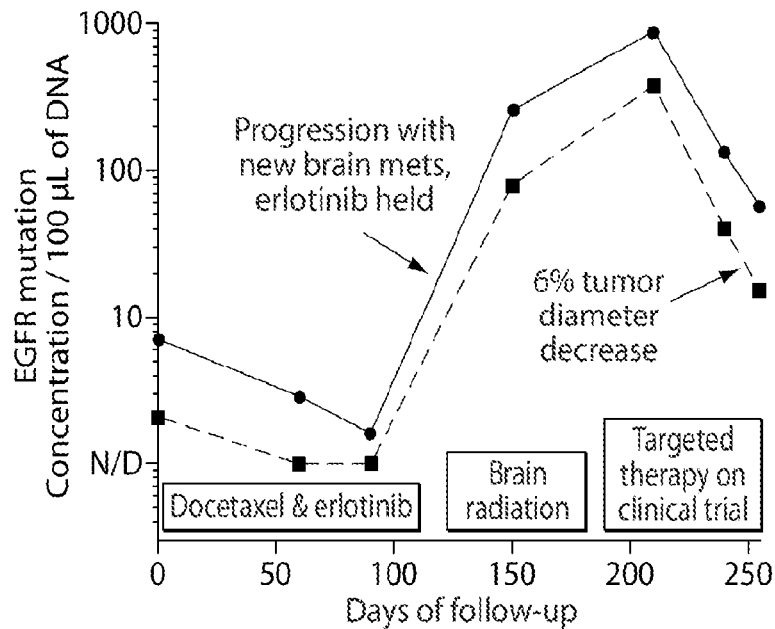
FIG. 11 demonstrates serial measurement of plasma genotype for disease monitoring. A wide dynamic range is seen in some cases (FIG. 11A, 11B). Decreases in plasma genotype can be seen both in cases of objective tumor shrinkage (FIG. 11A, 11D) and in cases of symptomatic response with no measurable disease (FIG. 11B, 11C). Concurrent EGFR L858R (FIG. 11A, solid line) and T790M (FIG. 11A, dashed line) mutations trend in parallel.
Figure 11B:
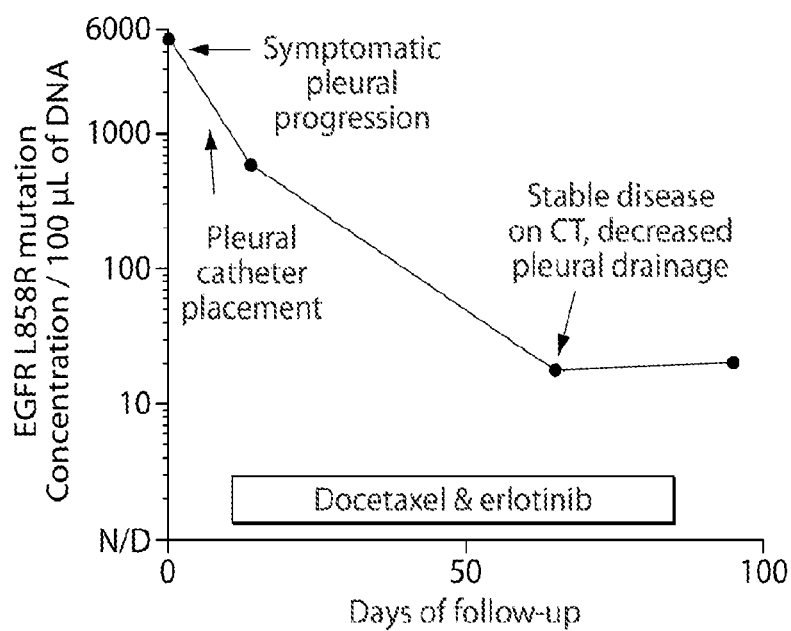
Figure 11C:
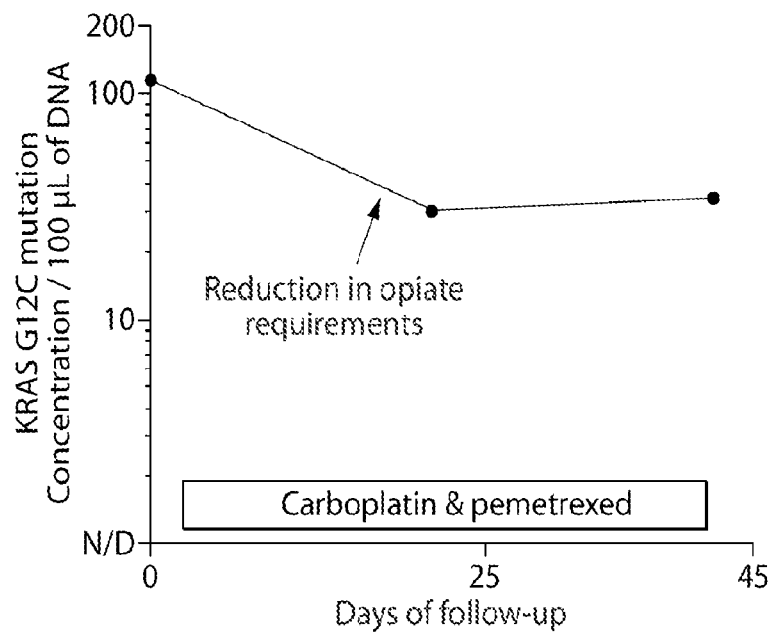
Figure 11D:
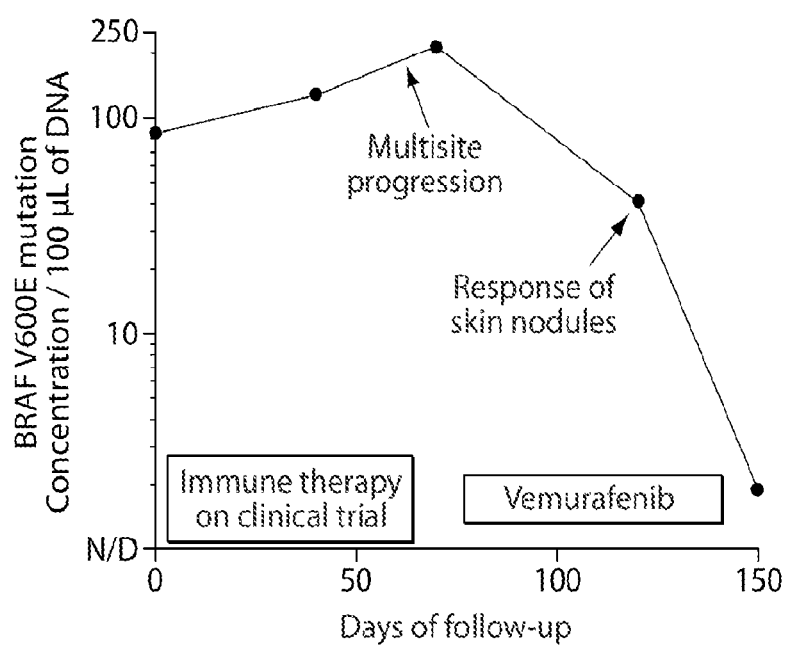
Figure 12A:
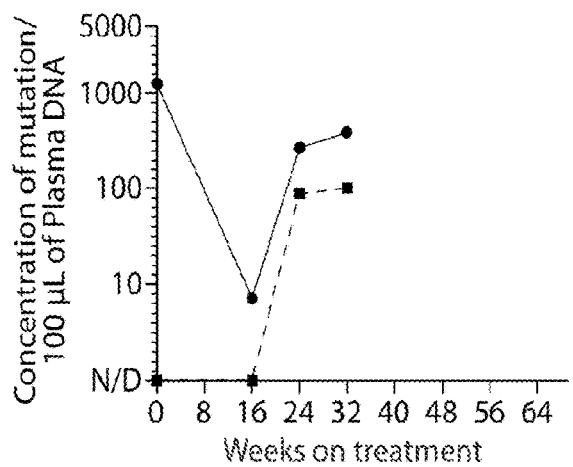
FIG. 12 shows plasma levels of mutant EGFR in 9 patients (FIG. 12A-12I) receiving first-line erlotinib until objective progression. In all patients, plasma levels of the EGFR sensitizing mutation (solid line) drop in response to treatment, with 8 patients (FIG. 12B-12I) having a complete plasma response. In 6 patients, plasma genotype levels reemerge up to 4 months prior to objective progression, and a lower concentration of T790M (dashed line) is also detected. In 3 patients (FIG. 12G-12I), plasma genotype was not detected at time of RECIST progression (PD); all 3 had indolent progression in the chest only.
Figure 12B:
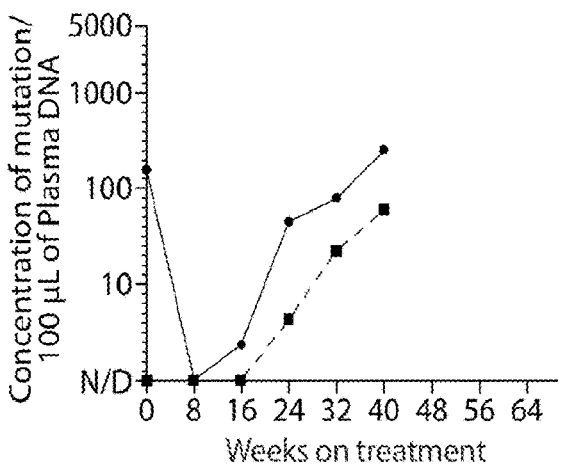
Figure 12C:
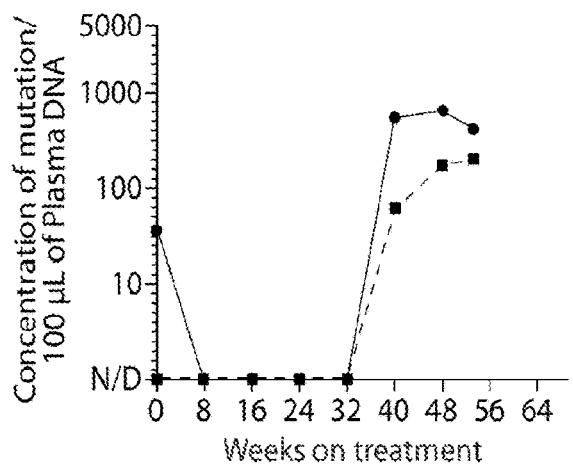
Figure 12D:
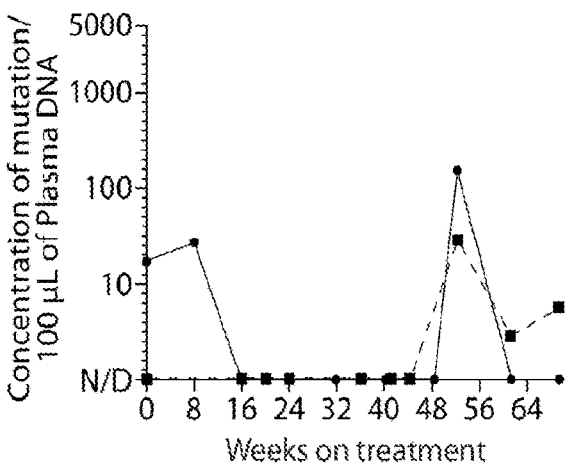
Figure 12E:
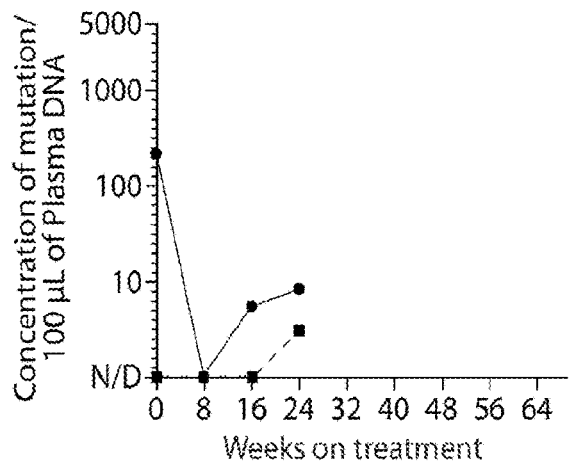
Figure 12F:
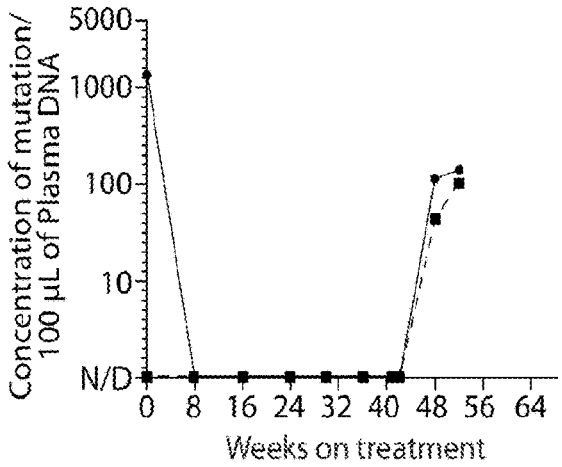
Figure 12G:
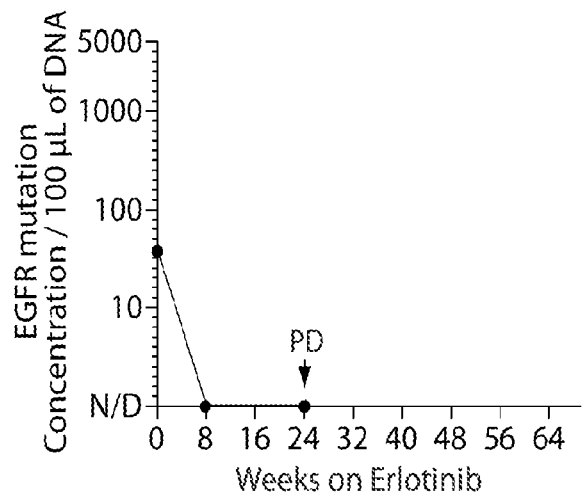
Figure 12H:
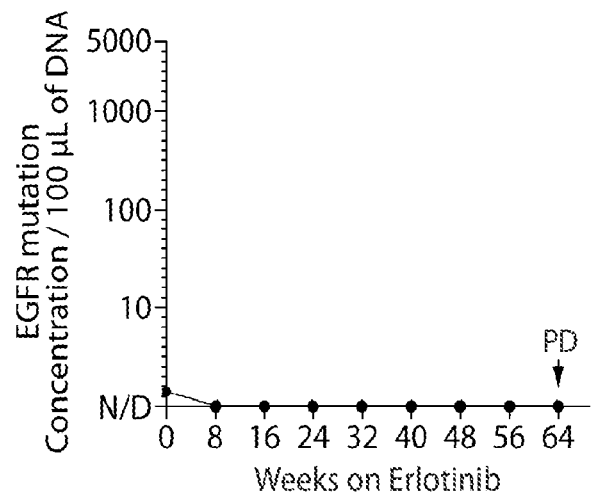
Figure 12I:
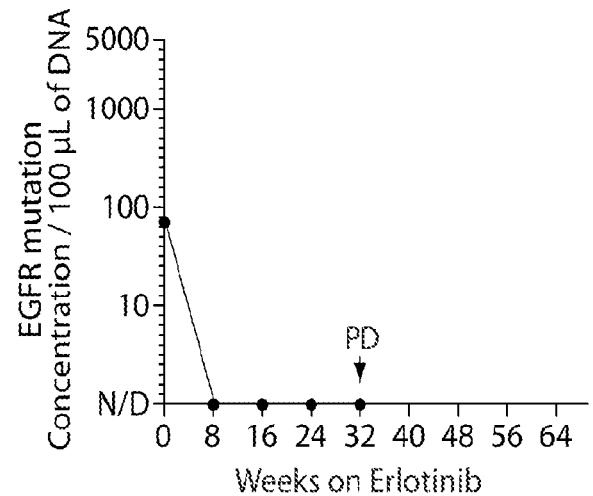

LINE-1 levels were next measured in plasma specimens from 38 EGFR-mutant and KRAS-mutant lung cancer patients studied in the above experiments. Detection of mutant alleles overall improved with increased levels of LINE-1 (FIG. 10B). In specimens with LINE-1 levels less than 3000 pg/µL, representing a low concentration of cfDNA, 50% had no detectable plasma genotype. Also observed was no detection of plasma genotype in cases with the highest levels of LINE-1 (greater than 700,000 pg/µL), likely indicating a high level of germline DNA obscuring detection of mutant cfDNA. However, when considering only cases with a LINE-1 concentration between 3000 and 700,000 pg/µL, sensitivity was 100% with 100% specificity (FIG. 10B), indicating that LINE-1 can be used for quality control to clarify which specimens are less likely to have a falsely negative result.

Developing a Disease Monitoring Biomarker

Figure 15:
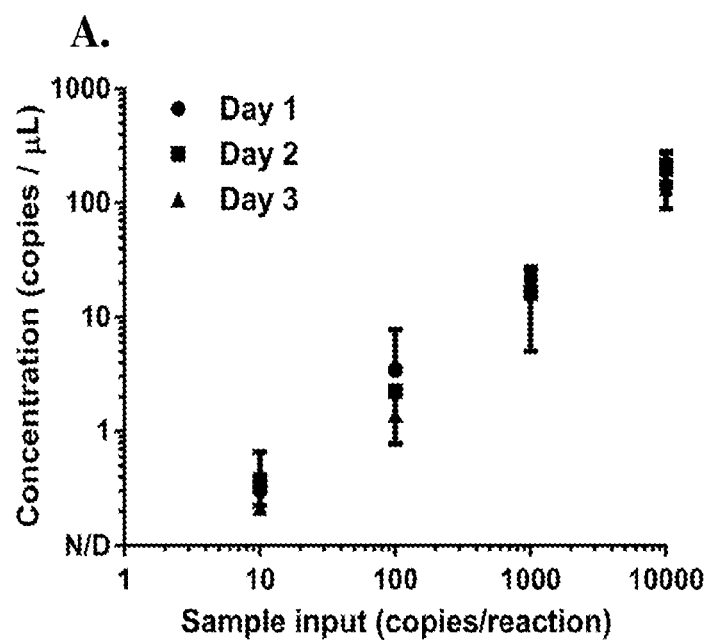
FIG. 15 shows inter- and intra-day variation of the ddPCR assay.
Figure 15:
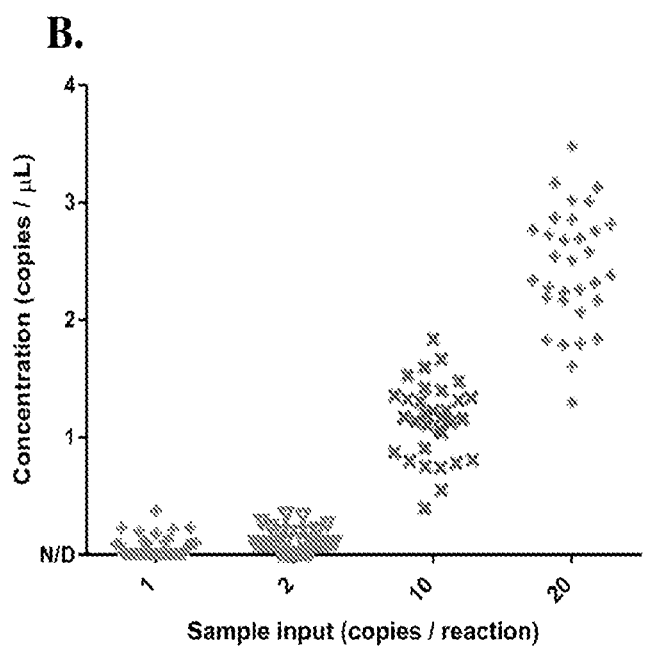

To assess the value of cfDNA genotype prevalence as a disease monitoring biomarker, the range of variability was quantified. Using the techniques described above, a fifth genotyping assay was developed to detect the EGFR T790M mutation. Human plasma DNA specimens were generated that contained either 1, 2, 10, or 20 copies of EGFR T790M per 25 µL reaction, divided each into 32 individual specimens, and each of these were tested for T790M prevalence by ddPCR. The assay exhibited a Poisson distribution between positives droplets and sample input with acceptable coefficient of variance in the range of 20-30% (FIG. 15), suggesting that changes exceeding this amount represent a true change in tumor burden or biology.

To gauge feasibility, serial plasma specimens were studied from patients with genotype-defined lung cancer or melanoma to determine whether changes in cfDNA were representative of tumor biology (FIG. 11). In a patient with EGFR-mutant NSCLC receiving chemotherapy after failing erlotinib (FIG. 11A), an increase in plasma L858R and T790M was seen with development of new brain metastases, followed by decreased plasma levels when treatment on a clinical trial was initiated. In a second case of EGFR-mutant NSCLC receiving chemotherapy (FIG. 11B), plasma L858R decreased as the patient's pleural drainage resolved, though CT imaging of the non-measurable disease showed disease stability. In a patient with KRAS-mutant NSCLC and bone metastases (FIG. 11C), chemotherapy caused a decrease in plasma G12C levels concordant with improved pain control and decreased opiate requirement. Lastly, a patient with BRAF-mutant melanoma had progression on experimental immune therapy followed by response to vemurafenib (FIG. 11D), seen in the rise and fall of plasma V600E levels. These experiments demonstrated that cfDNA genotyping has value for serial assessment of disease status, even in patients without objectively measurable disease on CT.

Monitoring for Resistance Mutations

To determine whether ddPCR could identify the development of resistance mutations after treatment with targeted therapy, patients were studied with advanced EGFR-mutant NSCLC treated on a prospective clinical trial of first-line erlotinib (NCT00997334), limiting the analysis to 13 patients that had serial plasma specimens collected until development of objective progression per the Response Evaluation Criteria In Solid Tumors (RECIST). In each of these patients, genotyping of archived tissue at diagnosis identified an EGFR exon 19 deletion without evidence of T790M. Four patients had no detectable pretreatment plasma genotype and were excluded, leaving 9 cases (69%) for analysis.

All 9 patients exhibited a plasma response to erlotinib, with 8 demonstrating a complete plasma response (FIG. 12). In 6 of the patients, plasma levels of mutant EGFR were again detected at objective progression, with plasma progression detected 4-12 weeks prior to RECIST progression. In each of these patients, plasma T790M could also be identified at progression, generally at somewhat lower levels than the EGFR sensitizing mutation. Four of these patients had a tumor rebiopsy adequate for EGFR genotyping, and T790M was confirmed in each. The remaining three patients had no reemergence of plasma genotype at objective progression; notably, each of these patients had indolent asymptomatic progression in the chest only, such that they subsequently continued single-agent erlotinib off-protocol.

Discussion

Described herein is a new quantitative assay for plasma-based tumor genotyping which has been technically optimized for translation into clinical practice. By quantifying the prevalence of targetable genotypes in clinical plasma specimens, and through study of rigorous gold-standard negative cases harboring non-overlapping cancer genotypes, a normal range has been identified for EGFR and KRAS mutation detection using ddPCR. Using such a calculated threshold as the criteria for a positive results, as well as LINE-1 concentration to eliminate poor quality specimens, the data demonstrates that this assay has high sensitivity and specificity.

Because many targetable genotypes are relatively uncommon, assay development was focused on maximizing specificity. Consider, for example, a plasma assay for detecting EGFR sensitizing mutations, present in 8.6% of 10,000 NSCLC patients from the large French experience (Barlesi F, Blons H, Beau-Faller M, Rouquette I, Ouafik Lh, Mosser J, et al. Biomarkers (BM) France: Results of routine EGFR, HER2, KRAS, BRAF, PI3KCA mutations detection and EML4-ALK gene fusion assessment on the first 10,000 non-small cell lung cancer (NSCLC) patients (pts). ASCO Meeting Abstracts. 2013; 31:8000). In this population, a plasma assay for EGFR mutations having 80% sensitivity and 90% or 95% specificity would have a PPV of only 43% or 60%, respectively. For this reason, a clinical-grade assay will likely need to sacrifice sensitivity in order to optimize specificity. In the same population, an assay with 70% sensitivity and 99% or 100% specificity would result in a PPV of 87% or 100%, respectively. Furthermore, the need to maximize specificity is magnified when testing for rarer genotypes such as BRAF V600E in NSCLC, representing only 2% of patients. One valuable characteristic of a quantitative assay such as ddPCR is the flexibility to allow an alteration of the criterion for positive if the pretest probability changes (e.g. Asian lung cancer patients). This is in contrast to an allele-specific PCR assay, such as one which showed high concordance with tumor genotyping in a preliminary analysis of plasma from 241 Asian lung cancer patients (Mok T, Wu Y L, Lee J S, Yu C-J, Sriuranpong V, Wen W, et al. Detection of EGFR-activating mutations from plasma DNA as a potent predictor of survival outcomes in FASTACT 2: A randomized phase III study on intercalated combination of erlotinib (E) and chemotherapy (C). ASCO Meeting Abstracts. 2013; 31:8021); as such an assay is qualitative, it cannot easily be adjusted to a higher specificity criterion in populations with lower mutation prevalence.

This study allows identification of the acquisition of plasma T790M in lung cancer patients prior to clinical development of resistance to EGFR kinase inhibitors. This has particular importance given the growing role of EGFR T790M as a biomarker for patients with EGFR-mutant lung cancer and acquired resistance. Firstly, acquired T790M has been associated with indolent growth and a favorable prognosis compared to T790M-negative acquired resistance. Secondly, third-generation EGFR kinase inhibitors with T790M-specific activity have recently been shown to induce responses in some patients. While pharmaceutical development of T790M-directed targeted therapies could be limited by the challenges of performing a repeat biopsy after resistance develops, the data described herein indicates that emergence of EGFR T790M can be identified noninvasively using ddPCR, and potentially used to guide subsequent treatment.

The quantitative nature of plasma genotyping with ddPCR also offers a mechanism for monitoring the prevalence of tumor clones harboring a specific genotype, potentially giving insight into the pharmacodynamics of a targeted therapy. In liquid malignancies like chronic myelogenous leukemia, rapidity of molecular response to kinase inhibitors has been established as an important biomarker of prognosis, and helps indicate which patients may need early salvage therapy. Similarly, plasma response to targeted therapies may prove to be valuable biomarker for genotype-defined solid tumors, both as a clinical biomarker of favorable outcome and potentially as an early clinical trial endpoint. Indeed, this was demonstrated in the small series described herein—the one patient not exhibiting a complete plasma response to erlotinib had early progression. In addition, response assessment using plasma genotype quantification could potentially allow trial accrual for those patients with genotype-defined solid tumors that are not objectively measurable using conventional response criteria.

Methods

Patients were identified from four IRB-approved protocols on the basis of (I) advanced NSCLC, (II) acquired resistance to an EGFR TKI, (III) possessing or having a planned re-biopsy and (IV) consent to research blood draws.

Baseline blood samples were collected from each patient in a standard EDTA tube. A subset of patients initiating a new treatment at the time of initial draw underwent two subsequent blood draws after the first and second cycles of treatment. Plasma was prepared using a modified protocol to minimize cell rupture. cfDNA was extracted using the QIAmp circulating nucleic acid kit (Qiagen). Previously validated probes and ddPCR system (BioRads) were used to detect and quantify EGFR mutation concentration as previously described (Oxnard et al., Clinical Cancer Research, 2014). The threshold for a positive test result was specific to each EGFR mutation studied: exon 19 del=6 copies/mL, L858R=1 copy/mL, T790M=0.5 copies/mL Patient characteristics are shown in Table 2.

TABLE 2

Patient characteristics
N = 45

| | | |
|---|---|---|
| Median age | 57 | (26-80) |
| Sex | | |
| Female | 36 | (80%) |
| Male | 9 | (20%) |
| Stage | | |
| IV | 41 | (91%) |
| Recurrent | 4 | (9%) |
| Distant metastases | | |
| Brain | 7 | (15%) |
| Bone | 21 | (47%) |
| Visceral | 10 | (22%) |
| Sensitizing mutation | | |
| Exon 19 del | 33 | (73%) |
| L858R | 9 | (20%) |
| Other | 3 | (7%) |
| Treatment (N = 12)† | | |
| Chemotherapy | 2 | |
| Immunotherapy | 1 | |
| Investigational drug therapy | 9 | |

†For patients starting a new therapy with serial plasma collected.

TABLE 3

| | PPV[1] | Specificity[2] | Sensitivity[3] |
|---|---|---|---|
| EGFR T790M | | | |
| All stage IV | 95% (19/20)[4] | 93% (13/14)[4] | 73% (19/26) |
| Stage IVa | 100% (2/2) | 100% (8/8) | 67% (2/3) |

TABLE 3-continued

| | PPV[1] | Specificity[2] | Sensitivity[3] |
|---|---|---|---|
| Stage IVb | 94% (17/18) | 84% (5/6) | 73% (17/23) |
| EGFR sensitizing mutation[5] | | | |
| All stage IV | — | — | 58% (25/43) |
| Stage IVa | — | — | 36% (5/14) |
| Stage IVb | — | — | 69% (20/29) |

Figure 16A:
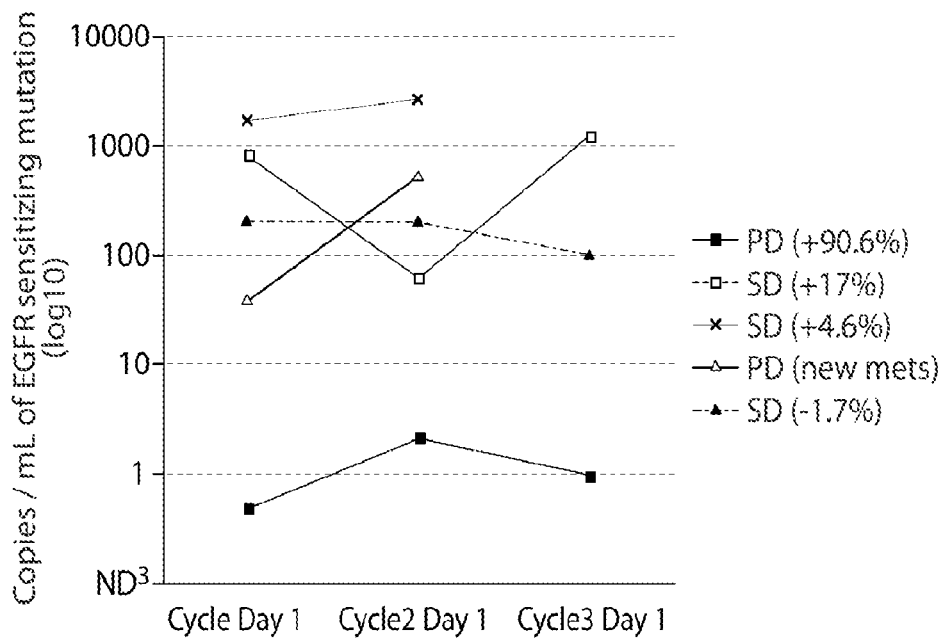
(FIG. 16A) Plasma genotype concentration is stable or increases in patients without evidence of a response.
Figure 16B:
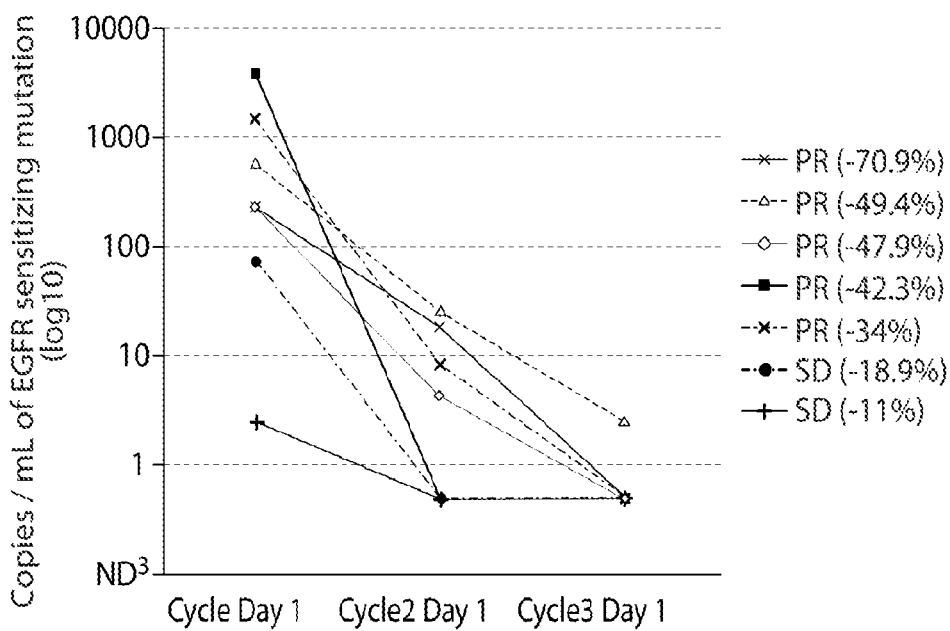
(FIG. 16B) In patients with at least a minor response to treatment, plasma genotype concentration[2] decreases an average of 1773 fold. [1]Minor response is defined as >10% reduction in tumor mass on initial re-staging CT scan. [2]Includes both EGFR exon 19 del and L858R depending on individual patient genotype. [3]A threshold for detectable EGFR mutation was set as 0.5 copies/mL for serial monitoring.

[1]Positive predictive value (PPV) = true positive/(true positive + false positive)
[2]Specificity = true negative/(true negative + false positive)
[3]Sensitivity = true positive/(true positive + false negative)
[4]Single false positive case had 4 copies/mL of T790M and 208 copies/mL of exon 19 del, with exon 19 del only on pleural biopsy
[5]EGFR exon 19 del & L858R, as all patients were mutation positive, specificity and positive predictive value cannot be calculated Results In patients with at least a minor response to treatment (defined as >10% reduction in tumor mass on initial re-staging CT scan), plasma genotype concentration (includes both EGFR exon 19 del and L858R depending on individual patient genotype) decreases an average of 1773 fold (FIG. 16B). Plasma genotype concentration is stable or increases in patients without evidence of a response (FIG. 16A). The sensitivity of ddPCR-based plasma genotyping may be better in patients with extra-thoracic metastases (stage IVb).

Case Report: Plasma Genotyping Directed Treatment

Figure 17:
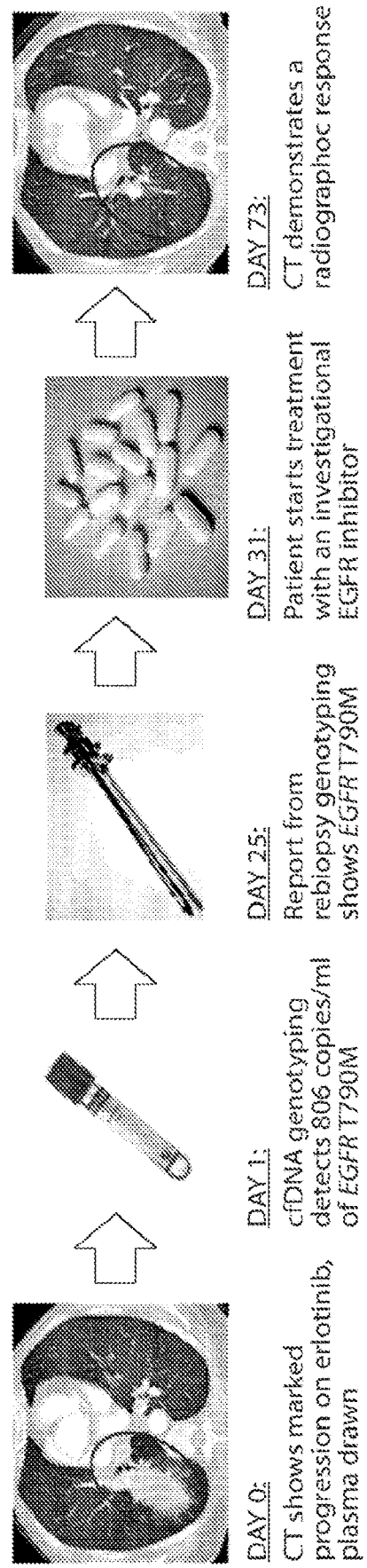
FIG. 17 shows a case report of a patient undergoing plasma genotyping directed treatment

Plasma genotyping in a patient with acquired resistance to EGFR TKI detects EGFR T790M 24 days earlier than re-biopsy and tissue genotyping. On Day 0, when CT shows marked progression on erlotinib, plasma is drawn (FIG. 17). On DAY 1, cfDNA genotyping detects 806 copies/ml of EGFR T790M. On DAY 25, report from rebiopsy genotyping shows EGFR T790M. Thus, this technology has the potential to allow treatment to begin weeks earlier without the risks of a biopsy. On DAY 31, Patient starts treatment with an investigational drug therapy. On DAY 73, CT demonstrates a radiographic response In conclusion, described herein is a cfDNA genotyping assay that is optimized for clinical application. Droplet Digital PCR has a rapid turnaround time, can be performed on routine plasma specimens, is relatively inexpensive, and provides results with a wide dynamic range, making it a an attractive tool for both clinical care and for clinical research.

REFERENCES

1. Paez J G, Janne P A, Lee J C, Tracy S, Greulich H, Gabriel S, et al. EGFR Mutations in Lung Cancer: Correlation with Clinical Response to Gefitinib Therapy. Science. 2004; 304:1497-500.
2. Kwak E L, Bang Y-J, Camidge D R, Shaw A T, Solomon B, Maki R G, et al. Anaplastic Lymphoma Kinase Inhibition in Non-Small-Cell Lung Cancer. N Engl J Med. 2010; 363:1693-703.
3. Flaherty K T, Puzanov I, Kim K B, Ribas A, McArthur G A, Sosman J A, et al Inhibition of Mutated, Activated BRAF in Metastatic Melanoma. N Engl J Med. 2010; 363:809-19.
4. Karapetis C S, Khambata-Ford S, Jonker D J, O'Callaghan C J, Tu D, Tebbutt N C, et al. Kras Mutations and Benefit from Cetuximab in Advanced Colorectal Cancer. N Engl J Med. 2008; 359:1757-65.
5. Jackman D M, Miller V A, Cioffredi L A, Yeap B Y, Janne P A, Riely G J, et al. Impact of epidermal growth factor receptor and KRAS mutations on clinical outcomes in previously untreated non-small cell lung cancer patients: results of an online tumor registry of clinical trials. Clin Cancer Res. 2009; 15:5267-73.
6. Maheswaran 5, Sequist L V, Nagrath 5, Ulkus L, Brannigan B, Collura C V, et al. Detection of mutations in EGFR in circulating lung-cancer cells. N Engl J Med. 2008; 359:366-77.
7. Misale S, Yaeger R, Hobor S, Scala E, Janakiraman M, Liska D, et al. Emergence of KRAS mutations and acquired resistance to anti-EGFR therapy in colorectal cancer. Nature. 2012; 486:532-6.
8. Higgins M J, Jelovac D, Barnathan E, Blair B, Slater S A, Powers P, et al. Detection of tumor PIK3C A status in Metastatic Breast Cancer using Peripheral Blood. Clin Cancer Res. 2012.
9. Diaz Jr L A Williams R T, Wu J, Kinde I, Hecht J R, Berlin J, et al. The molecular evolution of acquired resistance to targeted EGFR blockade in colorectal cancers. Nature. 2012; 486:537-40.
10. Dawson S J, Tsui D W, Murtaza M, Biggs H, Reda O M, Chin S F, et al. Analysis of circulating tumor DNA to monitor metastatic breast cancer. N Engl J Med. 2013; 368:1199-209.
11. Zhou Q, Zhang X-C, Chen Z-H, Yin X-L, Yang J-J, Xu C-R, et al. Relative Abundance of EGFR Mutations Predicts Benefit From Gefitinib Treatment for Advanced Non-Small-Cell Lung Cancer. J Clin Oncol. 2011; 29:3316-21.
12. Rago C, Huso D L, Diehl F, Karim B, Liu G, Papadopoulos N, et al. Serial assessment of human tumor burdens in mice by the analysis of circulating DNA. Cancer Res. 2007; 67:9364-70.
13. Vogelstein B, Kinzler K W. Digital PCR. Proc Natl Acad Sci USA. 1999; 96:9236-41.
14. Kuang Y, Rogers A, Yeap B Y, Wang L, Makrigiorgos M, Vetrand K, et al. Noninvasive detection of EGFR T790M in gefitinib or erlotinib resistant non-small cell lung cancer. Clin Cancer Res. 2009; 15:2630-6.
15. Hindson B J, Ness K D, Masquelier D A, Belgrader P, Heredia N J, Makarewicz A J, et al. High-Throughput Droplet Digital PCR System for Absolute Quantitation of DNA Copy Number. Anal Chem. 2011; 83:8604-10.
16. Cardarella S, Ortiz T M, Joshi V A, Butaney M, Jackman D M, Kwiatkowski D J, et al. The Introduction of Systematic Genomic Testing for Patients with Non-Small-Cell Lung Cancer. J Thorac Oncol. 2012; 7:1767-74 10.097/JTO.0b013e3182745bcb.
17. Johnson M L, Sima C S, Chaft J, Paik P K, Pao W, Kris M G, et al. Association of KRAS and EGFR mutations with survival in patients with advanced lung adenocarcinomas. Cancer. 2013; 119:356-62.
18. Barlesi F, Blons H, Beau-Faller M, Rouquette I, Ouafik Lh, Mosser J, et al. Biomarkers (BM) France: Results of routine EGFR, HER2, KRAS, BRAF, PI3KCA mutations detection and EML4-ALK gene fusion assessment on the first 10,000 non-small cell lung cancer (NSCLC) patients (pts). ASCO Meeting Abstracts. 2013; 31:8000.
19. Cardarella S, Ogino A, Nishino M, Butaney M, Shen J, Lydon C, et al. Clinical, pathological and biological features associated with BRAF mutations in non-small cell lung cancer. Clin Cancer Res. 2013.
20. Mok T, Wu Y L, Lee J S, Yu C-J, Sriuranpong V, Wen W, et al. Detection of EGFR-activating mutations from plasma DNA as a potent predictor of survival outcomes in FASTACT 2: A randomized phase III study on intercalated combination of erlotinib (E) and chemotherapy (C). ASCO Meeting Abstracts. 2013; 31:8021.
21. Oxnard G R, Arcila M E, Sima C S, Riely G J, Chmielecki J, Kris M G, et al. Acquired resistance to EGFR tyrosine kinase inhibitors in EGFR mutant lung cancer: Distinct natural history of patients with tumors harboring the T790M mutation. Clin Cancer Res. 2011; 17:1616-22.
22. Zhou W, Ercan D, Chen L, Yun C H, Li D, Capelletti M, et al. Novel mutant-selective EGFR kinase inhibitors against EGFR T790M. Nature. 2009; 462:1070-4.
23. Sequist L V, Soria J-C, Gadgeel S M, Wakelee H A, Camidge D R, Varga A, et al. First-in-human evaluation of CO-1686, an irreversible, selective, and potent tyrosine kinase inhibitor of EGFR T790M. ASCO Meeting Abstracts. 2013; 31:2524.
24. Arcila M E, Oxnard G R, Nafa K, Riely G J, Solomon S B, Zakowski M, et al. Rebiopsy of Lung Cancer Patients with Acquired Resistance to EGFR Inhibitors and Enhanced Detection of the T790M Mutation Using a Locked Nucleic Acid-Based Assay. Clin Cancer Res. 2011; 17:1169-80.
25. Branford S, Kim D W, Soverini 5, Haque A, Shou Y, Woodman R C, et al. Initial molecular response at 3 months may predict both response and event-free survival at 24 months in imatinib-resistant or -intolerant patients with Philadelphia chromosome-positive chronic myeloid leukemia in chronic phase treated with nilotinib. J Clin Oncol. 2012; 30:4323-9.

Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method to monitor cell free DNA comprising:
(i) obtaining a body fluid sample from a subject known to have a cancer characterized by a pair of mutually exclusive mutations specific to the cancer;
(ii) isolating cell free nucleic acids from the body fluid sample obtained from the subject;
(iii) measuring the level of Line 1 in the cell free nucleic acids isolated from the body fluid sample, wherein the level of Line 1 in the sample is within a range of 3,000-700,000 pg/μL;
(iv) measuring the amount of the first of the pair of mutually exclusive mutations specific to the cancer in the cell free nucleic acids isolated from the body fluid sample; and
(v) indicating in a report that the subject has the first of the pair of mutually exclusive mutations when (a) the level of Line 1 in the cell free nucleic acids isolated from the body fluid sample is within the range of 3,000-700,000 pg/μL and (b) the amount of the first of the pair of mutually exclusive mutations is increased as compared to a control amount,
wherein the control amount is the apparent amount of the first of the pair of mutually exclusive mutations in control cell free nucleic acids isolated from body fluid samples obtained from control subjects known to have the second of the pair of mutually exclusive mutations specific to the cancer using measuring conditions substantially the same as those used to measure the amount of the first of the pair of mutually exclusive mutations in the cell free nucleic acids isolated from the body fluid sample from the subject.

2. The method of claim 1, wherein the measuring of: the first of the pair of mutually exclusive mutations specific to the cancer in the cell free nucleic acids isolated from the body fluid sample obtained from the subject is performed by quantitative PCR, microarrays, Next-generation sequencing, chemiluminescence methods, fluorescent methods, digital detection, or mass spectrometry (MALDI-TOF).

3. The method of claim 1, wherein the cancer is lung cancer or colon cancer.

4. The method of claim 3, wherein the pair of mutually exclusive mutations is an epidermal growth factor receptor (EGFR) mutation and a Rat sarcoma (RAS) mutation, or wherein the pair of mutually exclusive mutations comprises an epidermal growth factor receptor (EGFR) mutation and a v-Ki-ras2 Kirsten rat sarcoma viral oncogene homolog (KRAS) mutation, or wherein the pair of mutually exclusive mutations comprises a v-raf murine sarcoma viral oncogene homolog B1 (BRAF) mutation and a Rat sarcoma (RAS) mutation.

5. The method of claim 4, wherein the EGFR mutation is selected from the group consisting of: L858R, T790M, L861Q, G719S, del 19 and exon 20 insertions.

6. The method of claim 4, wherein the KRAS mutation is G12C.

7. The method of claim 1, wherein the amount of the first of the pair of mutually exclusive mutations specific to the cancer is measured by digital droplet PCR.

8. The method of claim 1, wherein the amount of the first of the pair of mutually exclusive mutations is measured before and after administration of an anti-cancer therapy to the subject.

9. The method of claim 1, wherein step (i) step (iv) are repeated so as to monitor the subject's amount of the first of the pair of mutually exclusive mutations over time.

10. The method of claim 9, wherein a decrease in amount of the first of the pair of mutually exclusive mutations indicates that the cancer is stabilizing or decreasing, or wherein an increase in amount of the first of the pair of mutually exclusive mutations indicates that the cancer is increasing.

11. A method to monitor cell free DNA comprising:
(i) obtaining a body fluid sample from a subject known to have a cancer characterized by a pair of mutually exclusive mutations specific to the cancer;
(ii) isolating cell free nucleic acids from the body fluid sample obtained from the subject;
(iii) measuring the level of Line 1 in the cell free nucleic acids isolated from the body fluid sample, wherein the level of Line 1 in the sample is within a range of 3,000-700,000 pg/µL;
(iv) measuring the amount of the first of the pair of mutually exclusive mutations specific to the cancer in the cell free nucleic acids isolated from the body fluid sample;
(v) measuring the apparent amount of the first of the pair of mutually exclusive mutations in control cell free nucleic acids isolated from body fluid samples obtained from control subjects known to have the second of the pair of mutually exclusive mutations specific to the cancer using measuring conditions substantially the same as those used to measure the amount of the first of the pair of mutually exclusive mutations in the cell free nucleic acids isolated from the body fluid sample from the subject, and
(vi) indicating in a report that the subject has the first of the pair of mutually exclusive mutations when (a) the level of Line 1 in the cell free nucleic acids isolated from the body fluid sample is within the range of 3,000-700,000 pg/µL and (b) the amount of the first of the pair of mutually exclusive mutations is increased as compared to the apparent amount of the first of the pair of mutually exclusive mutations in control cell free nucleic acids isolated from body fluid samples obtained from control subjects.

12. A method to treat cancer comprising:
(i) obtaining a body fluid sample from a subject known to have a cancer characterized by a pair of mutually exclusive mutations specific to the cancer;
(ii) isolating cell free nucleic acids from the body fluid sample obtained from the subject;
(iii) measuring the level of Line 1 in the cell free nucleic acids isolated from the body fluid sample, wherein the level of Line 1 is within a range of 3,000-700,000 pg/µL;
(iv) measuring the amount of the first of the pair of mutually exclusive mutations specific to the cancer in the cell free nucleic acids isolated from the body fluid sample;
(v) measuring the apparent amount of the first of the pair of mutually exclusive mutations in control cell free nucleic acids isolated from body fluid samples obtained from control subjects known to have the second of the pair of mutually exclusive mutations specific to the cancer using measuring conditions substantially the same as those used to measure the amount of the first of the pair of mutually exclusive mutations in the cell free nucleic acids isolated from the body fluid sample from the subject; and
(vi) treating the subject with an anti-cancer therapy when (a) the level of Line 1 in the cell free nucleic acids isolated from the body fluid sample is within the range of 3,000-700,000 pg/µL and (b) the amount of the first of the pair of mutually exclusive mutations is increased as compared to the apparent amount of the first of the pair of mutually exclusive mutations in control cell free nucleic acids isolated from body fluid samples obtained from control subjects.

13. The method of claim 12, wherein step (i) step (iv) are repeated so as to monitor the subject's amount of the first of the pair of mutually exclusive mutations over time.

14. The method of claim 13, wherein administration of the anti-cancer therapy is maintained when the amount of the mutation decreases over time, or wherein the anti-cancer therapy is administered at a higher dosage or is changed when the amount of the mutation increases over time.

15. A method comprising:
(i) administering an anti-cancer therapy to a subject known to have a cancer characterized by a pair of mutually exclusive mutations specific to the cancer;
(ii) obtaining a body fluid sample from the subject;
(iii) isolating cell free nucleic acids from the body fluid sample obtained from the subject;
(iv) measuring the level of Line 1 in the cell free nucleic acids isolated from the body fluid sample, wherein the level of Line 1 in the sample is within a range of 3,000-700,000 pg/µL;
(v) measuring the amount of the first of the pair of mutually exclusive mutations specific to the cancer in the cell free nucleic acids isolated from the body fluid sample; and
(vi) measuring the apparent amount of the first of the pair of mutually exclusive mutations in control cell free nucleic acids isolated from body fluid samples obtained from control subjects known to have the second of the pair of mutually exclusive mutations specific to the cancer using measuring conditions substantially the same as those used to measure the amount of the first of the pair of mutually exclusive mutations in the cell free nucleic acids isolated from the body fluid sample from the subject.

16. The method claim 7, wherein the amount of the first of the pair of mutually exclusive mutations specific to the cancer is determined by:
preparing at least 2 serial dilutions of the cell free nucleic acids isolated from the body fluid sample;
measuring the amount of the first of the pair of mutually exclusive mutations in the at least 2 serial dilutions using digital droplet PCR; and
evaluating linearity of the measured dilutions to confirm accuracy of the method.

17. The method of claim 9, wherein an increase in amount of the mutation indicates that the cancer is increasing.

18. The method of claim 9, wherein the subject's amount of the first of the pair of mutually exclusive mutations is measured: (a) in a first sample obtained from the subject before the subject received an anti-cancer therapy; and (b) in a second sample obtained from the subject after the subject received an anti-cancer therapy.

19. The method of claim 11, wherein the measuring of: (a) the first of the pair of mutually exclusive mutations specific to the cancer in the cell free nucleic acids isolated from the body fluid sample obtained from the subject and (b) the apparent amount of the first of the pair of mutually exclusive mutations in cell free nucleic acids isolated from control body fluid samples obtained from control subjects known to have the second of the pair of mutually exclusive mutations specific to the cancer is performed by microarrays, Next-generation sequencing, chemiluminescence methods, fluorescent methods, digital detection, or mass spectrometry (MALDI-TOF).

20. A method to monitor cell free DNA comprising:
(i) obtaining a body fluid sample from a subject known to have a cancer characterized by a pair of mutually exclusive mutations specific to the cancer;

(ii) isolating cell free nucleic acids from the body fluid sample obtained from the subject;

(iii) measuring the level of Line 1 in the cell free nucleic acids isolated from the body fluid sample, wherein the measured level of Line 1 is within a range of 3,000-700,000 pg/μL of body fluid;

(iv) measuring the amount of the first of the pair of mutually exclusive mutations specific to the cancer in the cell free nucleic acids isolated from the body fluid sample; and (v) measuring the apparent amounts of the first of the pair of mutually exclusive mutations in control cell free nucleic acids isolated from body fluid samples obtained from a plurality of control subjects known to have the second of the pair of mutually exclusive mutations specific to the cancer using measuring conditions substantially the same as those used to measure the amount of the first of the pair of mutually exclusive mutations in the cell free nucleic acids isolated from the body fluid sample from the subject; and (vi) indicating a result in a report wherein: the amount measured in (iv) is greater than the highest amount measured in (v) and indicating in a report that the body fluid sample from the subject has the first of the pair of mutually exclusive mutations; or the amount measured in (iv) is less than the highest amount measured in (v) and indicating a report that the body fluid sample from the subject does not have the first of the pair of mutually exclusive mutations.

21. The method of claim 20, wherein the measuring of: the first of the pair of mutually exclusive mutations specific to the cancer in the cell free nucleic acids isolated from the body fluid sample obtained from the subject is performed by quantitative PCR, microarrays, Next-generation sequencing, chemiluminescence methods, fluorescent methods, digital detection, or mass spectrometry (MALDI-TOF).

22. The method of claim 20, wherein the cancer is lung cancer or colon cancer.

23. The method of claim 20, wherein the pair of mutually exclusive mutations is an epidermal growth factor receptor (EGFR) mutation and a Rat sarcoma (RAS) mutation, or wherein the pair of mutually exclusive mutations comprises an epidermal growth factor receptor (EGFR) mutation and a v-Ki-ras2 Kirsten rat sarcoma viral oncogene homolog (KRAS) mutation, or wherein the pair of mutually exclusive mutations comprises a v-raf murine sarcoma viral oncogene homolog B1 (BRAF) mutation and a Rat sarcoma (RAS) mutation.

24. The method of claim 23, wherein the EGFR mutation is selected from the group consisting of: L858R, T790M, L861Q, G719S, del 19 and exon 20 insertions.

25. The method of claim 20, wherein the amount of the first of the pair of mutually exclusive mutations is measured before and after administration of an anti-cancer therapy to the subject.

26. The method of claim 20, wherein step (i)-step (iv) are repeated so as to monitor the subject's amount of the first of the pair of mutually exclusive mutations over time.

\* \* \* \* \*

UNITED STATES PATENT AND TRADEMARK OFFICE
CERTIFICATE OF CORRECTION

| | | |
|---|---|---|
| PATENT NO. | : 10,865,451 B2 | Page 1 of 1 |
| APPLICATION NO. | : 14/897269 | |
| DATED | : December 15, 2020 | |
| INVENTOR(S) | : Janne et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this
Thirteenth Day of December, 2022

*Katherine Kelly Vidal*

Katherine Kelly Vidal
*Director of the United States Patent and Trademark Office*